United States Patent
Houjou et al.

(10) Patent No.: US 8,715,523 B2
(45) Date of Patent: May 6, 2014

(54) HEAT STORAGE MATERIAL AND HEAT UTILIZATION SYSTEM USING THE SAME

(75) Inventors: Hirohiko Houjou, Tokyo (JP); Hajime Shingai, Tokyo (JP); Katsunori Iwase, Kariya (JP)

(73) Assignees: The University of Tokyo, Tokyo (JP); Denso Corporation, Kariya (JP)

( * ) Notice: Subject to any disclaimer, the term of this patent is extended or adjusted under 35 U.S.C. 154(b) by 0 days.

(21) Appl. No.: 13/362,679

(22) Filed: Jan. 31, 2012

(65) Prior Publication Data

US 2012/0193570 A1  Aug. 2, 2012

(30) Foreign Application Priority Data

Jan. 31, 2011 (JP) ................................. 2011-018872
Nov. 25, 2011 (JP) ................................. 2011-257712

(51) Int. Cl.
| | |
|---|---|
| *C09K 5/00* | (2006.01) |
| *C09K 3/18* | (2006.01) |
| *E04B 1/74* | (2006.01) |
| *H01B 1/02* | (2006.01) |
| *C07F 1/00* | (2006.01) |
| *C07F 15/00* | (2006.01) |

(52) U.S. Cl.
USPC .............. 252/74; 252/62; 252/518.1; 252/70; 252/71; 556/110; 556/113; 556/130; 556/138; 556/146

(58) Field of Classification Search
USPC ........... 252/62, 70, 71, 75, 500, 518.1, 519.5, 252/521.2, 584; 556/110, 112, 113, 118, 556/121, 122, 123, 128, 130, 134, 138, 140, 556/141, 146
See application file for complete search history.

(56) References Cited

U.S. PATENT DOCUMENTS 3,094,583 A * 6/1963 Eich et al. .................... 174/25 R
3,361,711 A * 1/1968 Cyba et al. .................... 524/237
(Continued)

FOREIGN PATENT DOCUMENTS

| JP | 5-32963 | 2/1993 |
|---|---|---|
| JP | 2001-107035 | 4/2001 |

(Continued)

OTHER PUBLICATIONS

Houjou et al. Chemistry Letters, vol. 38, No. 5, 2009. published online Mar. 28, 2009.*

(Continued)

*Primary Examiner* — Peter F Godenschwager
*Assistant Examiner* — Jane L Stanley
(74) *Attorney, Agent, or Firm* — Oblon, Spivak, McClelland, Maier & Neustadt, L.L.P.

(57) ABSTRACT

There is provided a heat storage material capable of recovering/storing thermal energy such as exhaust heat energy or sunlight, and a heat utilization system using the same. The heat storage material of the present invention comprises a complex compound of the formula (I), wherein, R, R', A, B, C, D, A', B', C' and D' are as defined herein.

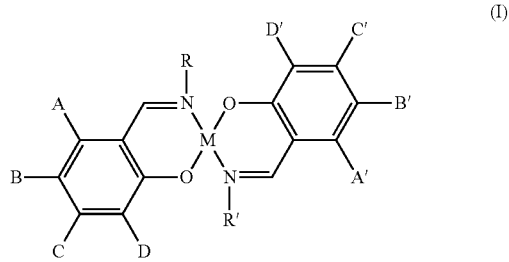

2 Claims, 25 Drawing Sheets
(5 of 25 Drawing Sheet(s) Filed in Color)

(56) References Cited

U.S. PATENT DOCUMENTS

| | | | |
|---|---|---|---|
| 3,843,536 A * | 10/1974 | Johnston | 508/550 |
| 4,136,097 A * | 1/1979 | Maryanoff | 548/562 |
| 4,233,035 A * | 11/1980 | Allen et al. | 44/420 |
| 4,245,018 A * | 1/1981 | Hara et al. | 430/14 |
| 4,383,835 A * | 5/1983 | Preuss et al. | 8/602 |
| 5,453,526 A * | 9/1995 | Pinnavaia et al. | 556/32 |
| 5,843,333 A * | 12/1998 | Hakemi | 252/299.5 |
| 6,713,435 B2 * | 3/2004 | Katsuki et al. | 504/260 |
| 8,076,500 B2 * | 12/2011 | Sundermeyer et al. | 560/24 |
| 8,431,750 B2 * | 4/2013 | Maliverney et al. | 568/432 |
| 2008/0193700 A1 * | 8/2008 | Wolleb et al. | 428/64.4 |
| 2011/0033741 A1 * | 2/2011 | Welter | 429/111 |

FOREIGN PATENT DOCUMENTS

| | | |
|---|---|---|
| JP | 2005-97530 | 4/2005 |
| JP | 2006-219557 | 8/2006 |

OTHER PUBLICATIONS

Hoshino et al., Inorg. Chem. 1990, 29, 5129-5131.*

Hoshino et al. Inorg. Chem. 1998, 37, 882-889. published online Mar. 9, 1998.*

Hara et al. Cryst. Growth. Des. 2011, 11, 5113-5121, published Oct. 3, 2011.*

* cited by examiner

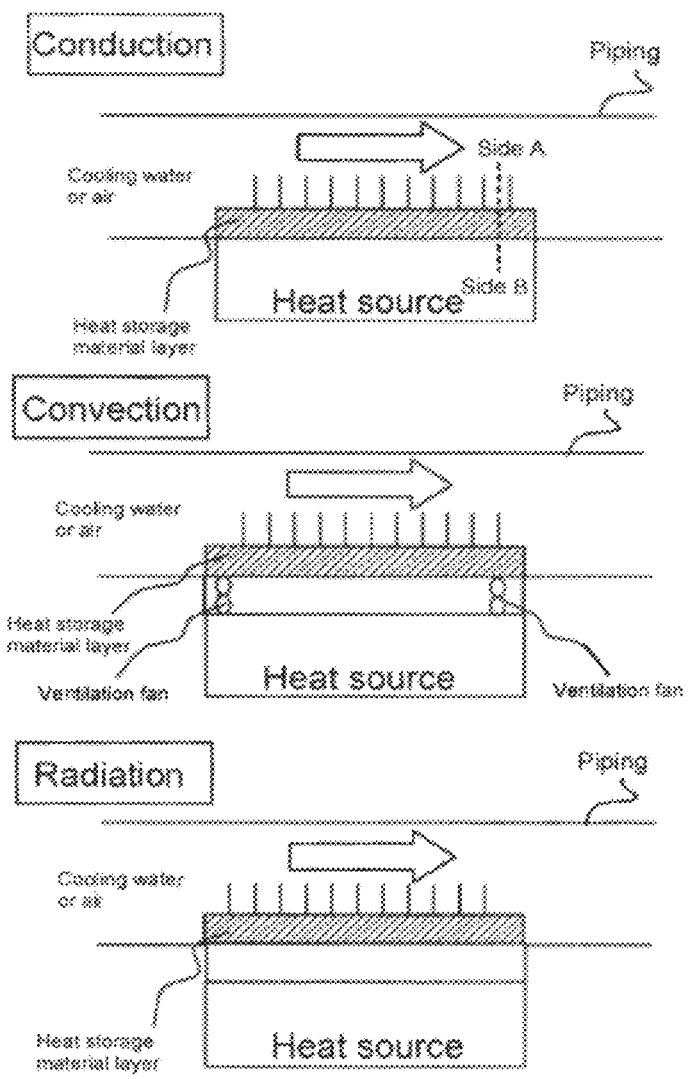

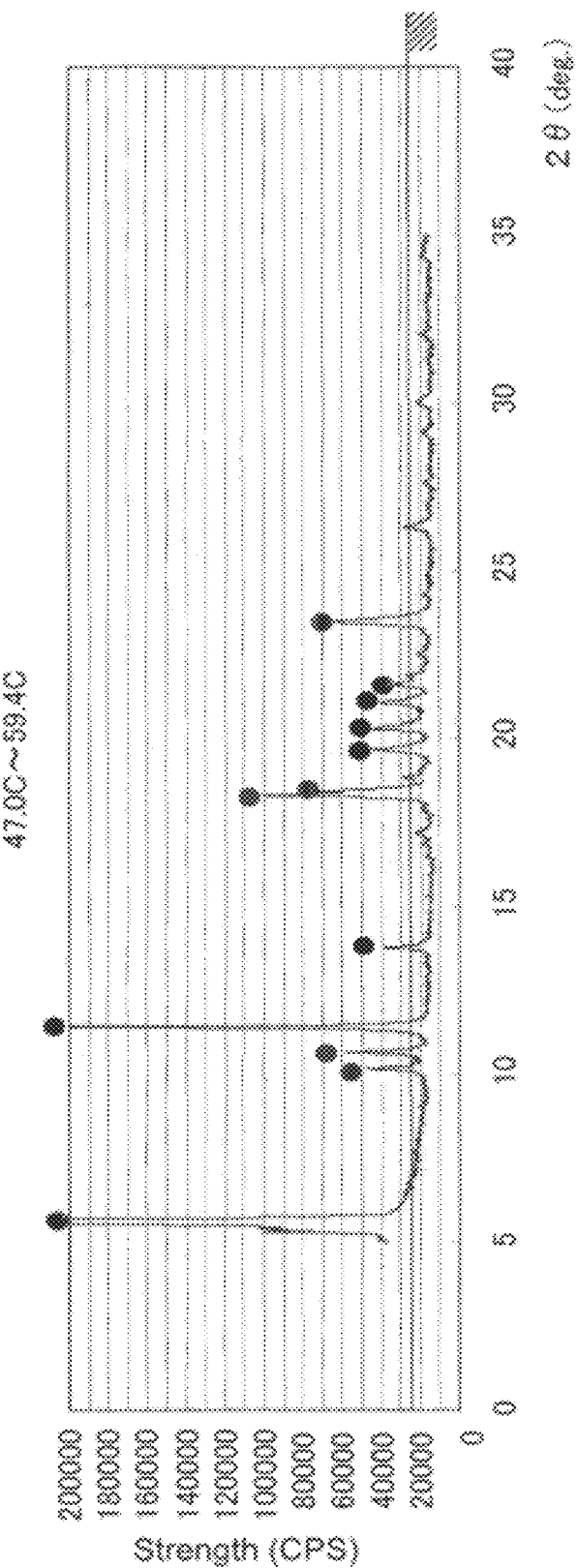

HEAT STORAGE MATERIAL AND HEAT UTILIZATION SYSTEM USING THE SAME

TECHNICAL FIELD

The present invention relates to use of a complex compound as a heat storage material, a complex compound in a novel crystal form and use thereof as a heat storage material, and a heat utilization system using such heat storage material.

BACKGROUND OF THE INVENTION

Conventionally, there has been a demand for utilization of surplus heat generated from automobiles or thermal energy of sunlight (e.g., electromagnetic wave of longer wavelength than the near-infrared). Generally, there was a problem that a scene where a heat is generated (time) and a scene where the heat is (or is desired to be) utilized do not necessarily coincide with each other in time.

For example, in the case of getting in an automobile during winter season, if exhaust heat such as heat generated during driving could be utilized for warming up the engine when getting in the automobile next time (e.g., the next morning), it would bring many advantages. For example, shorter initial warm-up time enables less fuel consumption at the time of engine start, that is, a fuel consumption rate can be improved. Further, immediate use of air heating at almost the same timing as getting in the automobile is also a merit for increasing the comfortability for automobile occupants.

Taking housing as an example, if thermal energy of sunlight in daytime could be utilized for any time after sunset (e.g., night of the day, night of the next day, etc.), then the costs of lighting and heating could be cut down.

One approach for solving the aforementioned problems to enjoy these advantages is a method for storing energy by means of a heat storage material utilizing a material of which three states can change in accordance with temperature increase.

As such heat storage materials, there were conventionally those using sodium pyrophosphate, an ionic liquid, glacial acetic acid, erythritol or the like (Patent Documents 1 to 4).

PRIOR ARTS

Patent Documents

[Patent Document 1] Japanese Unexamined Patent Publication No. 2001-107035
[Patent Document 2] Japanese Unexamined Patent Publication No. 2006-219557
[Patent Document 3] Japanese Unexamined Patent Publication No. 2005-97530
[Patent Document 4] Japanese Unexamined Patent Publication No. Hei 5-32963

BRIEF SUMMARY OF THE INVENTION

Problems to be Solved by the Invention

The conventional heat storage material as mentioned above stores heat by utilizing latent heat held by a material. However, for example, in the case of utilizing phenomena such as phase change (three states change) or return to the ground state from the disassociation state due to removal of thermal energy, there was a problem of loss of the stored heat at a temperature below one at which energy is stored, i.e., a problem that when the temperature of a heat storage material is lowered in such a state where heat is recovered (absorbed), then the amount of the energy stored is also lowered. Accordingly, there has been a strong demand for a heat storage material which recovers heat, and then generates heat by means of a trigger such as heat without being affected by external environments such as temperature decrease, and a heat utilization system using the same.

The present invention has been completed in view of the aforementioned circumstances, and has an object of providing a heat storage material capable of recovering/storing thermal energy such as exhaust heat energy or sunlight and a heat utilization system using the same.

Means for Solving the Problems

The present invention provides a heat storage material comprising a complex compound of the formula (I):

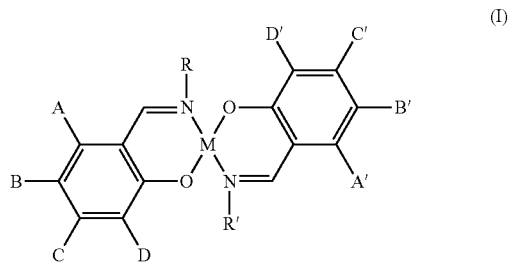

wherein,
R and R', each independently, are a linear or branched alkyl group having 1 to 18 carbons, or an optionally-substituted aryl group;
M is a divalent transition metal ion; and
A, B, C, D, A', B', C' and D' are hydrogen, or adjoining two of them are attached to each other, together with 2 carbon atoms to which they are attached, to form an optionally-substituted aryl ring.

Further, the present invention also provides a novel crystal form of the complex compound of the above formula (I) and a heat storage material comprising the same.

Furthermore, the present invention provides a heat utilization system comprising the aforementioned heat storage material.

Effect of the Invention

The complex compound of the formula (I) is capable of recovering/storing thermal energy such as exhaust heat energy, and thus it is possible to provide a heat storage material and a heat utilization system using the same.

The complex compound of the formula (I) changes the crystal structure with heat being absorbed. This means that the complex compound of the formula (I) changes its crystal structure by absorbing heat to store the energy.

Such complex compound is preferable, since this compound makes it possible to provide a heat storage material which is not affected by temperature change of the external environment in such a state where energy is absorbed/stored (of which amount of energy stored is not reduced due to temperature decrease of the external environment). Further, such complex compound is capable of releasing energy stored by giving a trigger, for example, thermal or physical/mechanical stimulation from the outside.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 9 is a schematic view of Embodiment 5 relating to a heat recovering/releasing portion provided with the heat storage material of the present invention.

FIG. 34 shows a powder X-ray diffraction spectrum of a complex compound S8Cu at 47.0° C. to 59.4° C. during Cycle 2. Circles in the diagram indicate a peak.

DETAILED DESCRIPTION OF THE INVENTION

Figure 1:
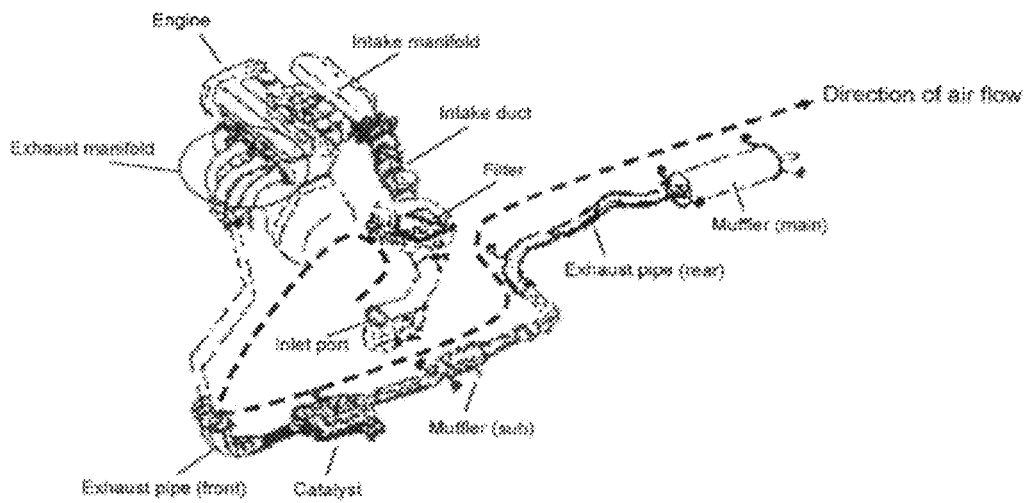
FIG. 1 is a schematic view showing the air flow in an engine.

Hereinafter, the present invention will be described in detail optionally with reference to the drawings, but the present invention is not limited thereto.

(Complex Compound)

Examples of a linear or branched alkyl group having 1 to 18 carbons in R and R' of the present invention include methyl, ethyl, n-propyl, or isopropyl, or linear or branched butyl, pentyl, hexyl, heptyl, octyl, nonyl, decyl, undecyl, dodecyl, tridecyl, tetradecyl, pentadecyl, hexadecyl, heptadecyl, or octadecyl.

An aryl group in R and R' of the present invention may have, for example, 5 to 16 ring members, preferably 6 to 10 ring members, and may have, for example, 1 to 4 rings, preferably 1 ring. Examples of such aryl group include a benzene ring, a naphthalene ring, an anthracene ring, and a pyrene ring, with a benzene ring, a naphthalene ring and the like being preferable in terms of solubility of a ligand. The aryl group in R and R' may be optionally substituted, and may either be unsubstituted, or substituted with an alkyl group such as a methyl group or an ethyl group or an aryl group such as a phenyl group.

In the complex compound of the formula (I), R and R' either may differ from each other or may be the same, but they are preferably the same in terms of easy synthesis.

In the present invention, any adjoining two of A, B, C, D, A', B', C' and D' may be attached to each other, together with 2 carbon atoms to which they are attached, to form an aryl ring. Such aryl ring may have, for example, 5 to 16 ring members, preferably 6 to 10 ring members, and may have, for example, 1 to 4 rings, preferably 1 ring. Examples of such aryl ring include a benzene ring, a naphthalene ring, an anthracene ring, and a pyrene ring, with a benzene ring, a naphthalene ring and the like being preferable in terms of solubility of a ligand.

This aryl ring may be optionally substituted, and may either be unsubstituted, or substituted with an alkyl group such as a methyl group or an ethyl group or an aryl group such as a phenyl group.

A complex compound of the aforementioned formula (I), wherein R and R' are a linear or branched alkyl group having 1 to 18 carbons, in particular, an octyl group; and A, B, C, D, A', B', C' and D' are hydrogen is preferable because it achieves a good heat storage effect.

A complex compound of the aforementioned formula (I), wherein R and R' are an aryl group, in particular, a phenyl group, which groups may either be unsubstituted or substituted with an alkyl group such as a methyl group or an ethyl group or an aryl group such as a phenyl group; A and B are attached to each other, together with 2 carbon atoms to which they are attached, to form an aryl ring, in particular, a benzene ring, and A' and B' are attached to each other, together with 2 carbon atoms to which they are attached, to form an aryl ring, in particular, a benzene ring; and C, D, C' and D' are hydrogen is preferable because it achieves a good heat storage effect.

The divalent transition metal ion of the present invention is not particularly limited, as long as it is attached (coordinated) to a 2-hydroxyphenyl-1-imine compound of the formula (III) or (III') described later which is a ligand, and it is preferably selected from transition metal elements of the fourth period of the periodic table, and is, particularly, zinc (II), copper (II), nickel (II), cobalt (II), manganese (II) and iron (II), among all, copper (II) or nickel (II).

In a complex compound of the formula (I) of the present invention, it is preferable that:
both R and R' are an octyl group, or are a phenyl group which is unsubstituted or substituted with a methyl group, an ethyl group or a phenyl group;
when R and R' are both an octyl group, A, B, C, D, A', B', C' and D' are hydrogen, or when R and R' are both a phenyl group which is unsubstituted or substituted with a methyl group, an ethyl group or a phenyl group, A and B are attached to each other, together with 2 carbon atoms to which they are attached, to form a benzene ring, A' and B' are attached to each other, together with 2 carbon atoms to which they are attached, to form a benzene ring, and C, D, C' and D' are hydrogen; and M is zinc (II), copper (II), nickel (II) or iron (III), in particular, copper (II) or nickel (II), because a good heat storage effect is achieved.

A process for preparing a complex compound of the formula (I) of the present invention is not particularly limited, and the complex compound can be conveniently prepared according to the steps set forth in the following Schemes 1 to 3.

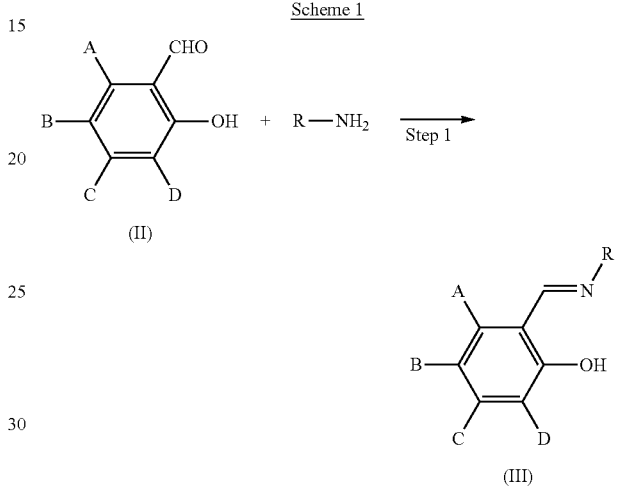

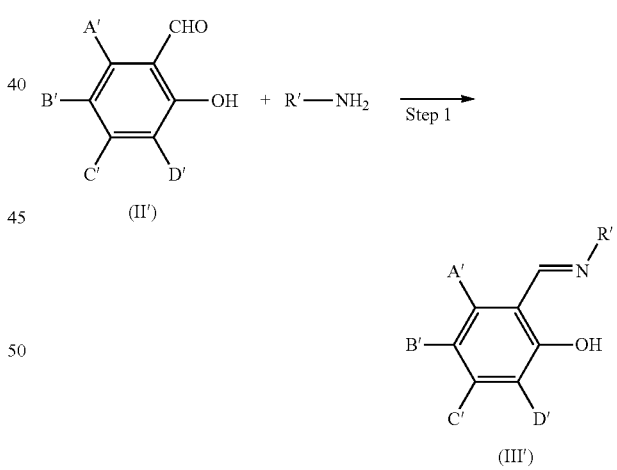

In Step 1 of the above Schemes 1 and 2, a 2-hydroxyphenyl-1-aldehyde compound of formula (II) or (II'), wherein, A, B, C, D, A', B', C' and D' are as defined in the above formula (I), is reacted with an amine compound: R—$NH_2$ or R'—$NH_2$ wherein R and R' are as defined in the above formula (I), including various alkyl amines or aromatic amines, for example, in an alcohol such as methanol or ethanol to synthesize a 2-hydroxyphenyl-1-imine compound (III or III'). The 2-hydroxyphenyl-1-aldehyde compound and the amine compounds as starting materials are both commercially available, or can be prepared according to a known method.

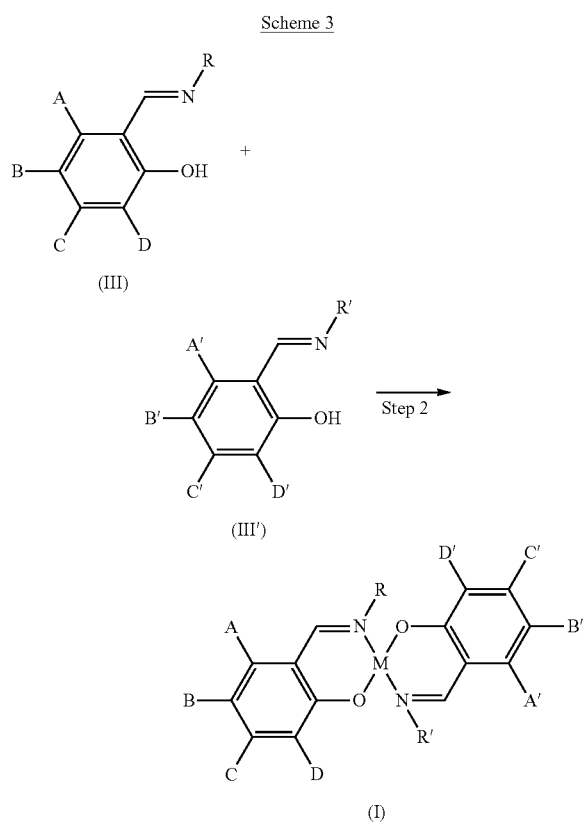

Scheme 3

(III)

(III')

Step 2

(I)

In Step 2 of the above Scheme 3, 2-hydroxyphenyl-1-imine compounds of the formulae (III) and (III') synthesized in the aforementioned Schemes 1 and 2 are dissolved, for example, in an organic solvent such as tetrahydrofuran or chloroform, an alcohol such as ethanol, or a mixed solvent thereof, for example, a mixed solvent of tetrahydrofuran and ethanol, to which a transition metal compound ($MX_2$), for example, a solution of a transition metal salt dissolved in an alcohol such as methanol or ethanol is added, whereby a hydrogen ion of a 2-hydroxyphenyl-1-imine compound (III and III') is exchanged with a transition metal ion to form a complex, and a precipitation occurs. Collection by filtration gives a complex compound (I) of the present invention.

For a heat storage material of the present invention, the resulting complex compound may be used as it is, or the purified one, for example, a crystal which may be deposited by dissolving the compound in a solvent such as tetrahydrofuran and then adding an appropriate amount of ethanol may be used.

In the present invention, the transition metal compound: $MX_2$ is not particularly limited, as long as it is capable of forming a complex compound of the formula (I) by supplying divalent transition metal ions, preferably, one which is selected from transition metals of the fourth period of the periodic table, particularly preferably, zinc (II), copper (II), nickel (II), cobalt (II), manganese (II) or iron (II) to a ligand of the formula (III) or (III'). Examples of the transition metal compound for use in the present invention include those which are used generally in the form of a salt of the aforementioned transition metal, for example, a low valent inorganic acid salt, organic acid salt, or complex salt of the aforementioned transition metal. Examples of such transition metal compound include, but not limited to, acetylacetone zinc (II), acetylacetone copper (II), acetylacetone nickel (II), acetylacetone cobalt (II), acetylacetone manganese (II), zinc (II) chloride, cobalt (II) chloride, iron (II) chloride, zinc (II) carbonate, cobalt (II) carbonate, manganese (II) carbonate, cobalt (II) oxide, zinc (II) acetate, copper (II) acetate, nickel (II) acetate, cobalt (II) acetate, manganese (II) acetate, zinc (II) stearate, cobalt (II) stearate, manganese (II) stearate, zinc (II) lactate or the like. It is preferable to use zinc (II) acetate, copper (II) acetate, nickel (II) acetate or iron (II) chloride.

(Heat Storage Material)

The heat storage material of the present invention either may be a complex compound of the formula (I) per se, or may be consist of two or more complex compounds of the formula (I), or may comprise together with one or more of the above complex compound other additives such as a binder for enhancing the film strength during thin film formation, or a metal or a carbon nanotube (CNT) for enhancing the thermal conductivity of a thin film, unless they impair the effect of the present invention. In particular, a heat storage material comprising two or more of the complex compounds is preferable because it reduces the number of a heating-cooling cycle until occurrence of heat storage phenomenon.

A process for manufacturing the heat storage material of the present invention is not particularly limited, for example, it can be manufactured by stirring and mixing one or more of the above complex compound and the above additive to be added as needed so as to be dispersed uniformly. This heat storage material may be filled into a suitable container, for example, a capsule-like container of the heat storage material (heat storage capsule) for use. As container materials of such heat storage capsule, plastics such as polypropylene, or metals such as aluminum or stainless can be used.

Hereinafter, an air-conditioning system for vehicles (Embodiments 1 to 3) and an air-conditioning system for housing (Embodiment 4) are described as the embodiments of the heat utilization system of the present invention, and the embodiments shown herein assume that heat higher than normal temperature is stored. The present invention is not limited thereto, since the heat storage material of the present invention is also capable of storing heat lower than normal temperature, that is, it may be also used as a cool storage material.

Before the descriptions of the systems, first, the air flow taken into an engine will be described with reference to FIG. 1. The air taken in from an inlet port is supplied to the inside of the engine from an intake manifold after dust removal with a filter. The supplied air is burned inside the engine together with a fuel, and an exhaust gas is exhausted from an exhaust manifold together with combustion heat. This exhaust is passed through the inside of an exhaust pipe to be discharged from a muffler after cleanup of the exhaust gas with a catalyst.

Figure 2:
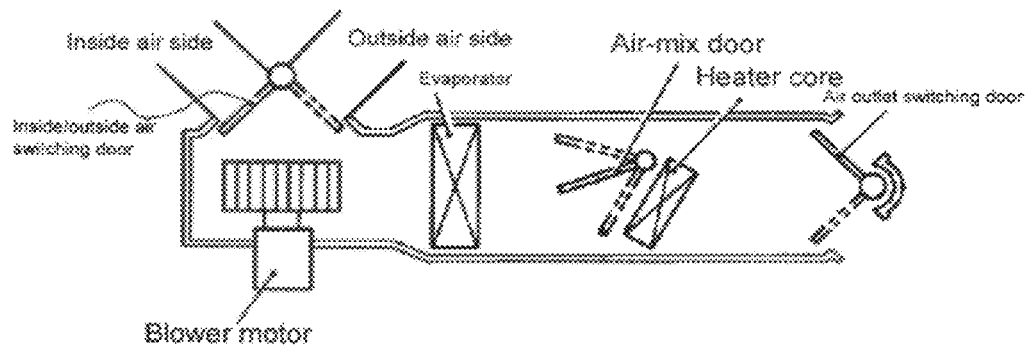
FIG. 2 is a schematic view of the section of an air conditioner.

Next, the air flow in an air conditioner will be described with reference to FIG. 2. As for the air flow, an air taken in from an inside/outside air switching door is sent by a blower fan, passed through an evaporator (cooling) and a heater core (heating), and subsequently supplied to the inside of a vehicle interior from an air outlet. The temperature of the air blown out is controlled by an air-mix door between the evaporator and the heater core. Further, according to the position of the inside/outside air switching door, air to be taken in can be selected from the inside or the outside of the vehicle interior. Generally, to take in air from the inside of the vehicle interior is referred to as "inside air mode", and to take in air from the outside air as "outside air mode".

Figure 3:
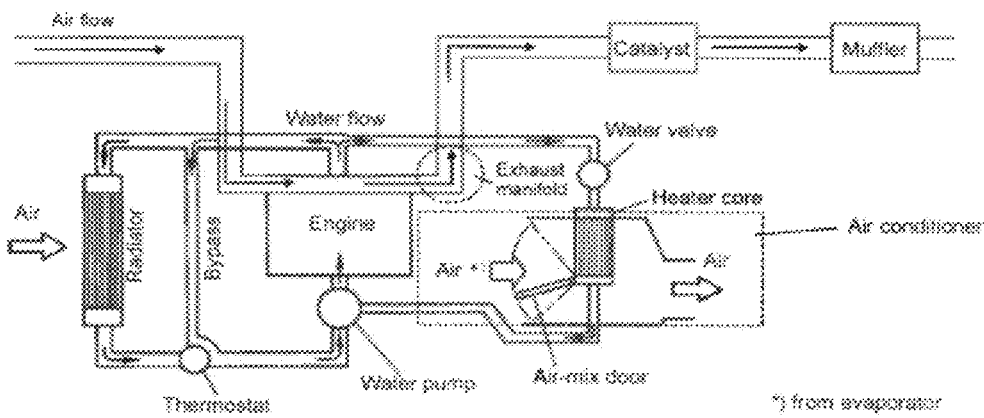
FIG. 3 is a schematic view showing the relationship between air flow and an air conditioner (in particular, heater).

Next, the air and water flow in an engine and an air conditioner (in particular, heater) will be described with reference to FIG. 3. The heat utilization system is intended to recover heat, in particular, exhaust heat, and reutilize it as heat. The "air flow" and "water flow" will be described simply from the viewpoint of a heater.

(Air Flow)

The air taken into the engine is discharged as an exhaust gas accompanied by combustion heat, due to combustion inside the engine. The temperature of the exhaust pipe is highest in the vicinity of the exhaust manifold, and the temperature becomes lower as closer to the muffler. The temperature of the exhaust pipe is about 500 to 600° C. at the exhaust manifold and 200 to 300° C. at the area between catalyst and the muffler during driving at steady state (e.g., during driving at a constant speed of 40 km/h).

(Water Flow)

Control is carried out such that heat generated from the engine is removed with cooling water, and, when the cooling water becomes higher than a desired temperature (measured by a thermostat), then heat is exhausted from a radiator, so as to maintain the cooling water so as to be constant. Air heating using an air conditioner is carried out by circulating a part of this cooling water to the heater core.

Embodiment 1

Figure 4:
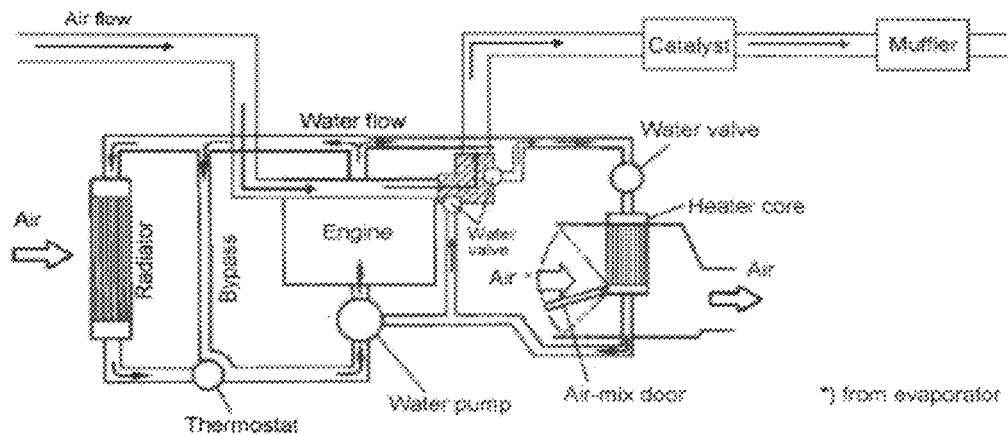
FIG. 4 is a schematic view of Embodiment 1 in which the exhaust heat of an engine is recovered from an exhaust manifold.

Description will be given for Embodiment 1 in which exhaust heat of the engine is recovered from an exhaust manifold, with reference to FIG. 4. The recovered heat is utilized as a heat source when the temperature of cooling water is lower such as at the time of engine start.

[Operation] During driving, the exhaust heat generated in the exhaust manifold is recovered with a heat recovering/releasing portion (diagonal line part in the drawing) provided with the heat storage material of the present invention. The aforementioned heat storage material is capable of retaining exhaust heat energy in the substance as a change of the crystal structure even after the engine is stopped. When the engine is started again (e.g., the next morning, etc.), the energy stored by the above heat storage material can be released, to heat the cooling water (air, in Embodiment 3).

[Effect] According to the location to which the recovered heat is supplied, two effects can be achieved. The first effect is mainly the case of heating a heater core. When the heater core is heated using a cooling water loop of the heater core from the aforementioned heat recovering/releasing portion, then air heating becomes possible immediately after the engine start. The second effect is the case of heating the cooling water around the engine. The supply of the heated cooling water to the engine brings not only an advantage of shorter warm-up idling time at the engine start, but also an advantage of more compact size (volume) of a catalyst layer in the downstream of "air flow".

Embodiment 2

Figure 5:
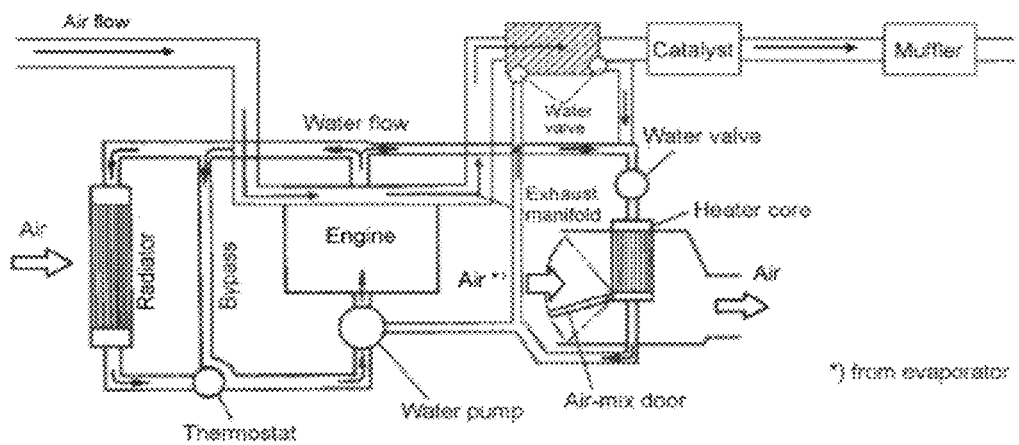
FIG. 5 is a schematic view of Embodiment 2 in which the exhaust heat of an engine is recovered from an exhaust pipe.

Description will be given for Embodiment 2 in which exhaust heat of the engine is recovered from the exhaust pipe, with reference to FIG. 5. The location at which the heat recovering/releasing portion provided with the heat storage material of the present invention is installed is preferably an area before a catalyst where the temperature of exhaust heat is high (diagonal line part in the drawing), but is not particularly limited, so that it can be installed at any area such as the exhaust manifold. The [Operation] and [Effect] are the same as in Embodiment 1.

Embodiment 3

Figure 6:
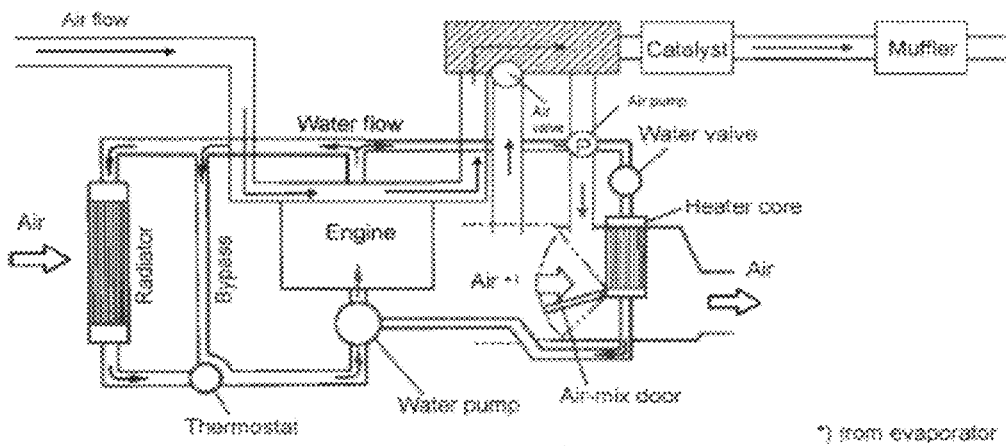
FIG. 6 is a schematic view of Embodiment 3 in which the exhaust heat of an engine is recovered from an exhaust pipe to warm up the air directly.

Description will be given for Embodiment 3 in which exhaust heat of the engine is recovered from the exhaust pipe to warm up the air directly, with reference to FIG. 6. The air to be warmed up is sucked in from the "air flow" of the air conditioner by means of an air pump, or the like, and is brought back into the air conditioner after heating. The location at which the air is brought back is preferably an area between the evaporator and the heater core. The location at which the heat recovering/releasing portion provided with the heat storage material of the present invention is installed is preferably an area where the temperature of exhaust heat is high, for example, an area before catalyst (diagonal line part in the drawing), but is not particularly limited, so that it can be installed at any area such as the exhaust manifold. The [Operation] is the same as in Embodiment 1. The [Effect] is that it is possible to warm up the air immediately after the engine start.

Embodiment 4

Figure 7:
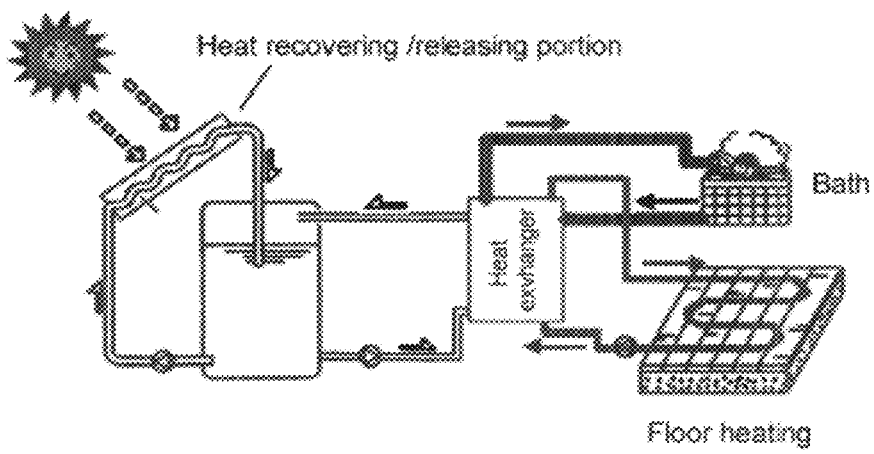
FIG. 7 is a schematic view of Embodiment 4 in which thermal energy of sunlight is recovered in housing.
Figure 8:
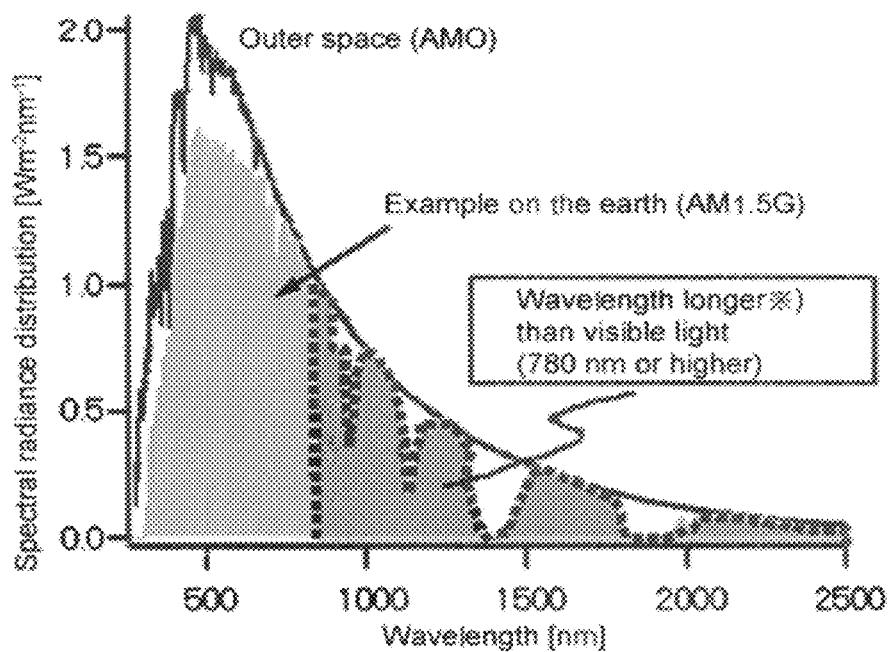
FIG. 8 is a diagram showing spectral radiance distribution of sunlight.

Description will be given for Embodiment 4 in which thermal energy of sunlight in housing is recovered, with reference to FIG. 7. The wavelength of a light to be utilized as thermal energy is a wavelength longer than 780 nm (FIG. 8). Accordingly, the mode in which thermal energy is received is radiation. The heat recovering/releasing portion provided with the heat storage material of the present invention receives sunlight, and recovers thermal energy from the sun. Subsequently, an energy stored by the aforementioned heat storage material is released at any time, so as to heat the cooling water, or utilize the heat for a bath or floor heating. The [Effect] is reduction of the costs of lighting and heating.

Embodiment 5

Description will be given for Embodiment 5 concerning a heat recovering/releasing portion provided with the heat storage material of the present invention, with reference to FIG. 9. A heat source with higher temperature is more preferable, but may be installed in any location such as the exhaust manifold. A mode of energy in which thermal energy from the heat source is transmitted to the aforementioned heat storage material could be any mode such as conduction, convection, and radiation.

In the case of using convection, it is preferably provided with a fan or the like for sufficiently stirring an air layer between the heat source and the aforementioned heat storage material layer. In radiation, it is preferable to provide the aforementioned heat storage material layer so as to be parallel with respect to the radiation surface of the heat source. The layer of air is provided in a space between the heat source and the heat storage material layer. The distance is not particularly limited, but may be determined such that the heat storage material has an optimum temperature. When an energy stored in the aforementioned heat storage material is released, and transmitted as heat to the cooling water or the air, it is preferable to provide a releasing side (Side A in the diagram of conduction) with a fin material for increasing the surface area in order to enhance an efficiency of heat-transfer.

EXAMPLES

Hereinafter, Examples will be shown to describe the present invention in detail, but these Examples are not intended to limit the present invention.

Example 1

6.88 g (40.0 mmol) of 2-hydroxy-1-naphthaldehyde was dissolved in 10 ml ethanol under heating, and 3.72 g (20.0 mmol) of aniline was added. After stirring under reflux at 70° C. for 1 hour, completion of the reaction was confirmed by TLC. Upon being left at rest over night in a refrigerator, a crystal was formed, and the resulting precipitation was filtered by Kiriyama funnel. Drying under reduced pressure at 25° C. for 24 hours gave 2-hydroxy-1-naphthylmethylidene aniline (hereinafter, also referred to as "HNA") as a yellow crystal (9.17 g, 93%). 0.99 g (4.00 mmol) of HNA was dissolved in 50 ml deaerated ethanol, and 50 ml of a deaerated ethanol solution of 0.40 g (2.00 mmol) of copper acetate monohydrate was added with stirring. Upon stirring under reflux at 70° C. for 1 hour, a precipitation was formed, and completion of the reaction was confirmed by TLC. The resulting precipitation was filtered by Kiriyama funnel, and washed sufficiently with ethanol. Drying under reduced pressure at 25° C. for 24 hours gave a crude product of a complex compound NACu of the following formula as a red-brown crystal (1.10 g, 98%). Further, a part of the resulting crystal was dissolved in tetrahydrofuran, and ethanol having a 4-fold volume thereof was added to deposit a crystal. This crystal was filtered and dried under reduced pressure to give a purified product of the complex compound NACu.

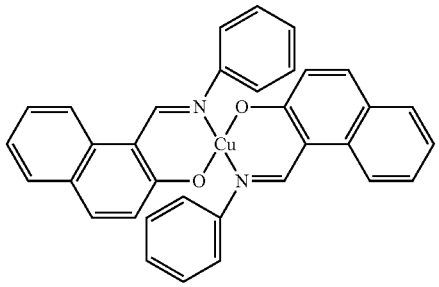

Example 2

0.13 g (1.0 mmol) of octylamine and 0.12 g (1.0 mmol) of salicylaldehyde were dissolved in 7.5 ml ethanol, and 5 ml of an ethanol solution of 0.10 g (0.5 mmol) of copper acetate monohydrate was added with stirring. After stirring under reflux at 70° C. for 1 hour, completion of the reaction was confirmed by TLC. The solvent was distilled off with an evaporator until the reaction solution was about 5 ml, which was subsequently left at rest over night in the refrigerator, whereupon a crystal was formed. Filtration by Kiriyama funnel was followed by sufficient washing with ethanol. Drying under reduced pressure at 25° C. for 24 hours gave a complex compound S8Cu of the following formula as a brown scale-like crystal (0.19 g, 72%).

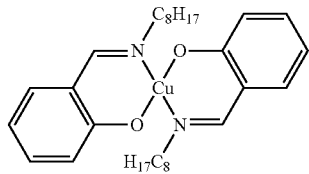

Example 3

3.44 g (20.0 mmol) of 2-hydroxy-1-naphthaldehyde was dissolved in 50 ml ethanol under heating, and 3.38 g (20.0 mmol) of 2-aminobiphenyl was added. After stirring under reflux at 70° C. for 1 hour, completion of the reaction was confirmed by TLC. The solution was concentrated with an evaporator to about 30 ml, whereupon a crystal was formed, which was filtered by Kiriyama funnel. Drying under reduced pressure at 25° C. for 24 hours gave 2-hydroxy-1-naphthylmethylidene-2-phenylaniline (hereinafter, also referred to as "HNBP") as a yellow crystal (5.62 g, 87%).

1.29 g (4.00 mmol) of HNBP was dissolved in a mixed solvent of 20 ml tetrahydrofuran and 30 ml ethanol, and 50 ml of an ethanol solution of 0.50 g (2.00 mmol) of nickel acetate tetrahydrate was added with stirring. Upon stirring under reflux at 70° C. for 1 hour, a crystal was deposited. Completion of the reaction was confirmed by TLC. The resulting crystal was filtered by Kiriyama funnel, and washed sufficiently with ethanol. Drying under reduced pressure at 25° C. for 24 hours gave a crude product of a complex compound NBPNi of the following formula as a green-brown crystal (1.35 g, 96%).

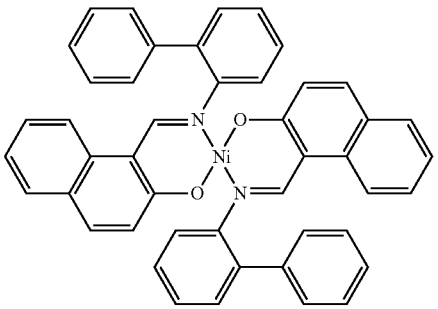

Example 4

3.44 g (20.0 mmol) of 2-hydroxy-1-naphthaldehyde was dissolved in 50 ml ethanol under heating, and 2.14 g (20.0 mmol) of o-toluidine was added. After stirring under reflux at 70° C. for 1 hour, completion of the reaction was confirmed by TLC. The solution was concentrated with an evaporator to about 30 ml, whereupon a crystal was formed, which was filtered by Kiriyama funnel. Drying under reduced pressure at 25° C. for 24 hours gave 2-hydroxy-1-naphthylmethylidene-2-methylaniline (hereinafter, also referred to as "HNOT") as a yellow crystal (4.24 g, 81%).

1.06 g (4.00 mmol) of HNOT was dissolved in a mixed solvent of 20 ml tetrahydrofuran and 30 ml ethanol, and 50 ml of an ethanol solution of 0.50 g (2.00 mmol) of nickel acetate tetrahydrate was added with stirring. Upon stirring under reflux at 70° C. for 1 hour, a crystal was deposited. Completion of the reaction was confirmed by TLC. The resulting crystal was filtered by Kiriyama funnel, and washed sufficiently with ethanol. Drying under reduced pressure at 25° C. for 24 hours gave a crude product of a complex compound NOTNi of the following formula as a green-brown crystal (1.04 g, 89%). A part of the resulting crystal was dissolved in tetrahydrofuran, and ethanol having a 4-fold volume thereof was added to deposit a crystal. This crystal was filtered, and dried under reduced pressure to give a purified product of the complex compound NOTNi.

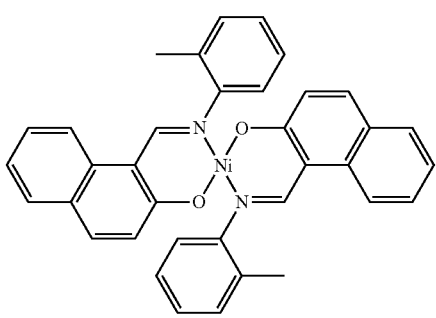

Example 5

3.44 g (20.0 mmol) of 2-hydroxy-1-naphthaldehyde was dissolved in 50 ml ethanol under heating, and 2.14 g (20.0 mmol) of m-toluidine was added. After stirring under reflux at 70° C. for 1 hour, completion of the reaction was confirmed by TLC. The solution was concentrated with an evaporator to about 30 ml, whereupon a crystal was formed, which was filtered by Kiriyama funnel. Drying under reduced pressure at 25° C. for 24 hours gave 2-hydroxy-1-naphthylmethylidene-3-methylaniline (hereinafter, also referred to as "HNMT") as a yellow crystal (4.43 g, 85%).

1.06 g (4.00 mmol) of HNMT was dissolved in a mixed solvent of 20 ml tetrahydrofuran and 30 ml ethanol, and 50 ml of an ethanol solution of 0.50 g (2.00 mmol) of nickel acetate tetrahydrate was added with stirring. Upon stirring under reflux at 70° C. for 1 hour, a crystal was deposited. Completion of the reaction was confirmed by TLC. The resulting crystal was filtered by Kiriyama funnel, and washed sufficiently with ethanol. Drying under reduced pressure at 25° C. for 24 hours gave a crude product of a complex compound NMTNi of the following formula as a green-brown crystal (0.98 g, 85%). A part of the resulting crystal was dissolved in tetrahydrofuran, and ethanol having a 4-fold volume thereof was added to deposit a crystal. This crystal was filtered, and dried under reduced pressure to give a purified product of the complex compound NMTNi.

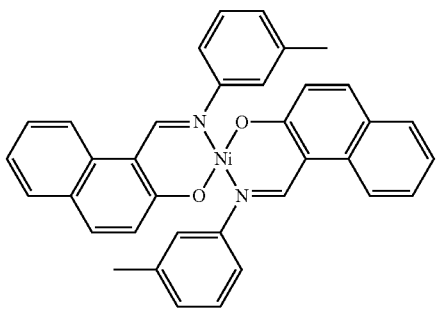

Example 6

6.88 g (40.0 mmol) of 2-hydroxy-1-naphthaldehyde was dissolved in 10 ml ethanol under heating, and 3.72 g (40.00 mmol) of aniline was added. After stirring under reflux at 70° C. for 1 hour, completion of the reaction was confirmed by TLC. Upon being left at rest over night in the refrigerator, a crystal was formed, and the resulting precipitation was filtered by Kiriyama funnel. Drying under reduced pressure at 25° C. for 24 hours gave 2-hydroxy-1-naphthylmethylidene aniline (hereinafter, also referred to as "HNA") as a yellow crystal (9.17 g, 93%).

0.99 g (4.00 mmol) of HNA was dissolved in 50 ml ethanol, and 50 ml of an ethanol solution of 0.50 g (2.00 mmol) of nickel acetate tetrahydrate was added with stirring. Upon stirring under reflux at 70° C. for 1 hour, a precipitation was formed, and completion of the reaction was confirmed by TLC. The resulting precipitation was filtered by Kiriyama funnel, and washed sufficiently with ethanol. Drying under reduced pressure at 25° C. for 24 hours gave a crude product of a complex compound NANi of the following formula as a green-brown crystal (1.03 g, 94%). A part of the resulting crystal was dissolved in tetrahydrofuran, and ethanol having a 4-fold volume thereof was added to deposit a crystal. This crystal was filtered, and dried under reduced pressure to give a purified product of the complex compound NANi.

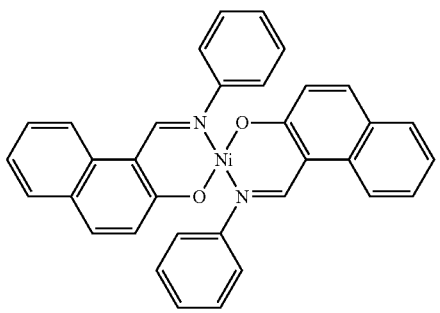

Example 7

3.44 g (20.0 mmol) of 2-hydroxy-1-naphthaldehyde was dissolved in 50 ml ethanol under heating, and 2.14 g (20.0 mmol) of p-toluidine was added. After stirring under reflux at 70° C. for 1 hour, completion of the reaction was confirmed by TLC. Upon concentration of the solution with an evaporator to about 40 ml, a crystal was formed, which was filtered by Kiriyama funnel. Drying under reduced pressure at 25° C. for 24 hours gave 2-hydroxy-1-naphthylmethylidene-4-methylaniline (hereinafter, also referred to as "HNPT") as a yellow crystal (4.70 g, 90%). 1.06 g (4.00 mmol) of HNPT was dissolved in a mixed solvent of 20 ml tetrahydrofuran and 30 ml ethanol, and 50 ml of an ethanol solution of 0.40 g (2.00 mmol) of copper acetate monohydrate was added with stirring. Upon stirring under reflux at 70° C. for 1 hour, a crystal was deposited. Completion of the reaction was confirmed by TLC. The resulting crystal was filtered by Kiriyama funnel, and washed sufficiently with ethanol. Drying under reduced pressure at 25° C. for 24 hours gave a crude product of a complex compound NPTCu of the following formula as a red-brown crystal (1.17 g, 94%). A part of the resulting crystal was dissolved in tetrahydrofuran, and ethanol having a 4-fold volume thereof was added to deposit a crystal. This crystal was filtered, and dried under reduced pressure to give a purified product of the complex compound NPTCu.

[Differential Scanning Calorimeter (DSC) Measurement]

In the present invention, DSC measurement was carried out using the following device and conditions.

Device: DSC3100SA, Bruker AXS K.K.

Sample container: aluminum open cell

Temperature range: 0 to 200° C.

Heating and cooling speed: 2 to 40° C./min.

Purge gas: $N_2$

Cooling system: liquid $N_2$

A complex compound produced in the aforementioned Example was dried, and about 5 to 8 mg thereof was weighed and placed in an aluminum open cell, and DSC measurement was carried out at a heating and cooling speed of 20° C./min. The results are shown in FIGS. 10 to 17.

In these results, an endothermic peak (melting) associated with melting was confirmed at the time of temperature rise in the first cycle. Further, at the time of cooling in this cycle, no peak indicating endotherm and exotherm was confirmed. In the second cycle, at the time of temperature rise, an exothermic peak (crystallization) was confirmed. Subsequently, when temperature was raised to the temperature of exothermic peak or higher, the similar endothermic peak (melting) was confirmed near the endothermic temperature found at the time of temperature rise in the first cycle.

Figure 15:
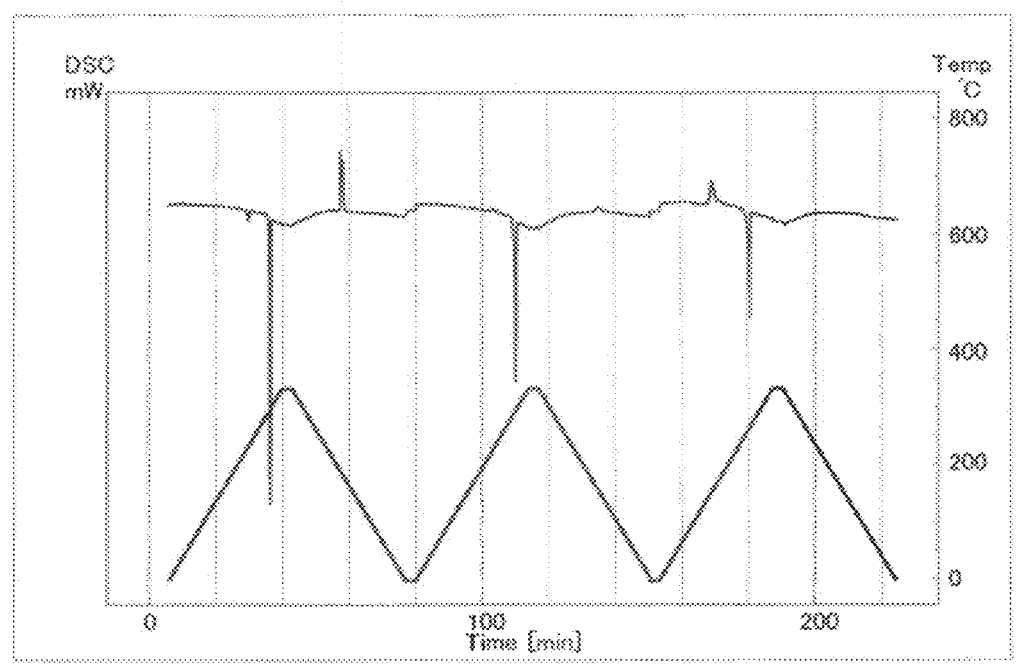
FIG. 15 shows in the upper part a DSC curve of a purified product of a complex compound NANi measured in a heating-cooling cycle indicated by a polygonal line in the lower part.
Figure 16:
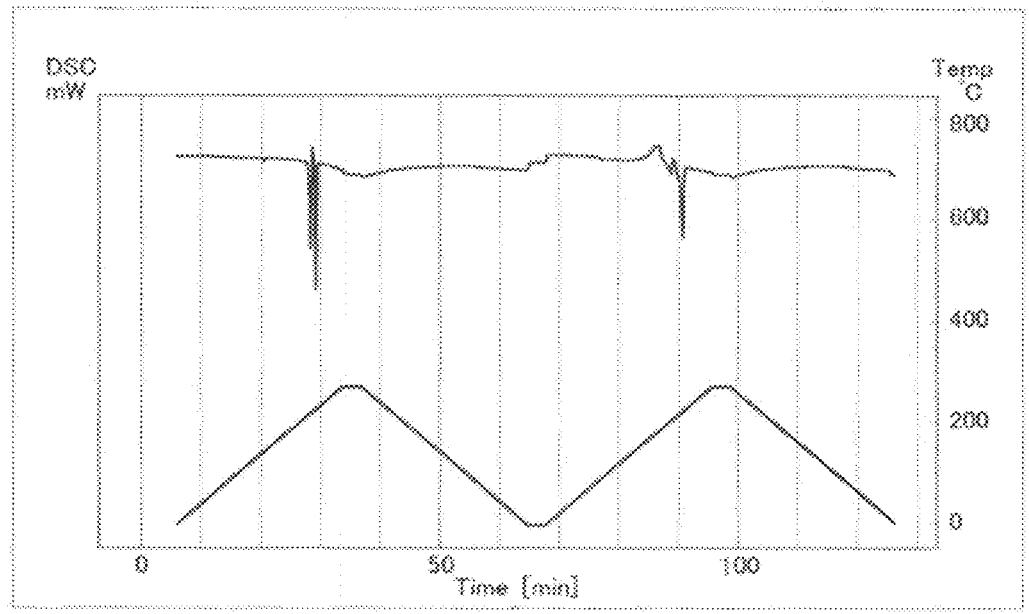
FIG. 16 shows in the upper part a DSC curve of a purified product of a complex compound NPTCu measured in a heating-cooling cycle indicated by a polygonal line in the lower part.
Figure 17:
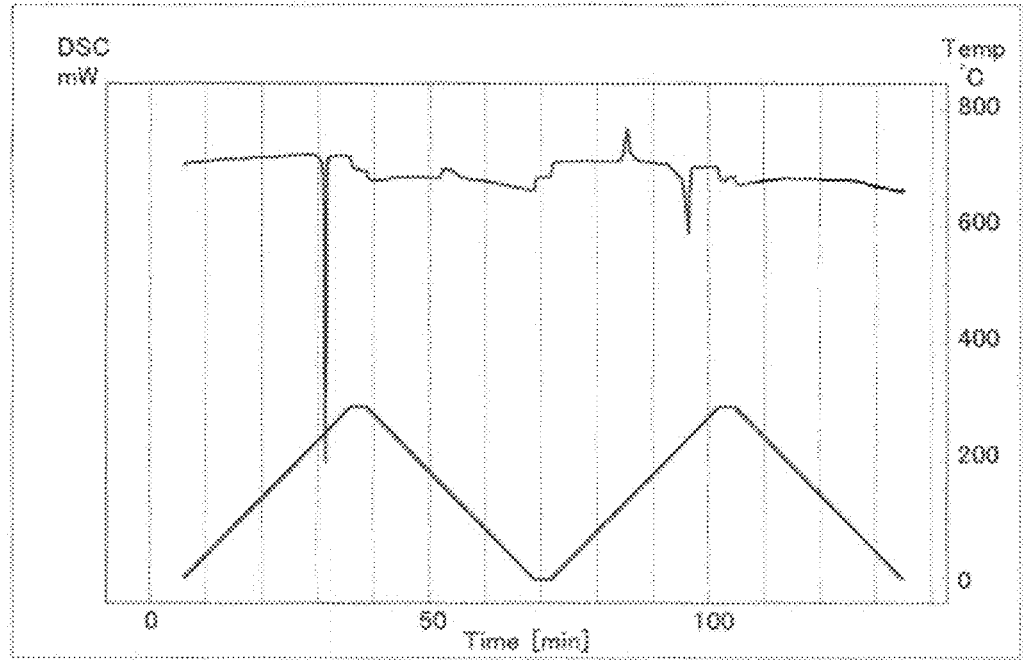
FIG. 17 shows in the upper part a DSC curve of a purified product of a complex compound NACu measured in a heating-cooling cycle indicated by a polygonal line in the lower part.

However, as for a purified product of a complex compound NaNi, a peak indicating endotherm was confirmed at the time of temperature rise, and a peak indicating exotherm at the time of cooling in the first cycle. In the second cycle, a peak indicating endotherm was confirmed at the time of temperature rise, and no peak indicating endotherm and exotherm was confirmed at the time of cooling. In addition, in the third cycle, an exothermic peak was confirmed at the time of temperature rise (FIG. 15).

In the conventional heat storage material utilizing latent heat, endotherm (melting) at the time of temperature rise and the ensuing exotherm (crystallization) at the time of cooling are confirmed as paired phenomena. In contrast, in the present invention, endotherm and exotherm are not paired. That is, it is possible to retain endotherm (store heat) at the time of temperature rise, and subsequently release the stored heat (also referred to herein as "heat storage phenomenon") at the time of temperature rise. Accordingly, it is possible to release stored thermal energy with heat as a trigger.

[Confirmation of Exotherm Associated with Crystallization Due to Mechanical Stimulation]

In the present invention, thermography measurement was carried out using the following device.

Manufacturer: FLIR SYSTEMS

Instrument name: FLIR SC620

Figure 18:
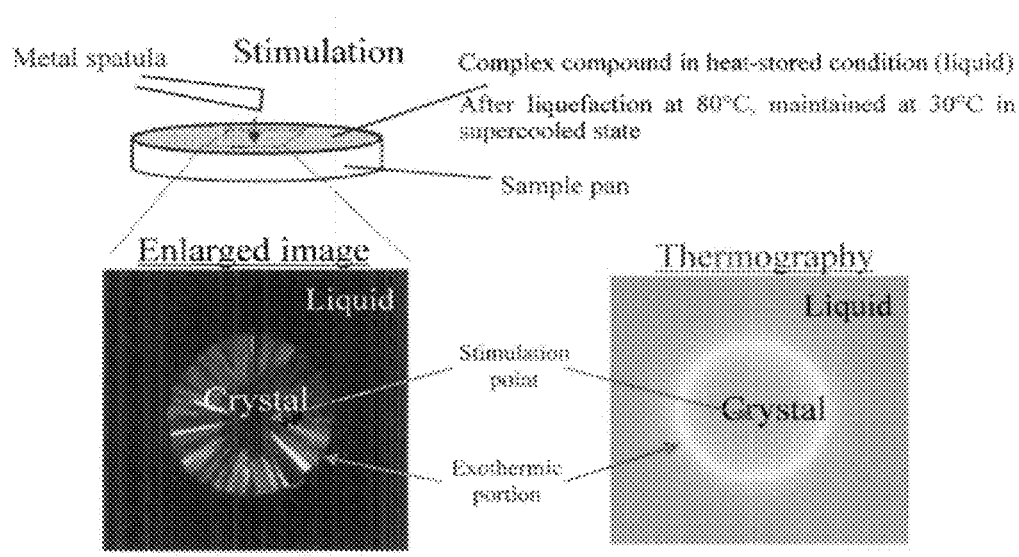
FIG. 18 shows an enlarged image and a thermographic image of crystallization of a complex compound S8Cu caused by mechanical stimulation. In the diagrams, the enlarged image and thermographic image show, respectively, the state of crystallization of the complex compound S8Cu and a thermal distribution associated with this crystallization. Further, the stimulation point indicates a point on the complex compound S8Cu prodded with a metal spatula, and the crystal, liquid and exothermic portion indicate, respectively, a crystal portion, a liquid portion, and a exothermic portion of the complex compound S8Cu.

A certain amount of a complex compound S8Cu obtained in Example 2 was taken up in a sample pan, liquidized at 80° C., and subsequently maintained at 30° C. in a supercooled state. Mechanical stimulation was given to this liquid complex compound S8Cu in the supercooled state by prodding it with a metal spatula, thereupon circular crystallization with this stimulation point as the center was confirmed by visual observation (enlarged image in FIG. 18). Furthermore, occurrence of exotherm in the circumferential part of this crystal was also confirmed (thermography in FIG. 18). This exotherm demonstrates that the complex compound S8Cu was crystallized due to physical or mechanical stimulation to release heat (FIG. 18).

Accordingly, the complex compound of the present invention was recognized to be capable of releasing thermal energy stored also by means of a trigger other than heat, for example, physical or mechanical stimulation.

[DSC Measurement of Mixture]

Figure 19:
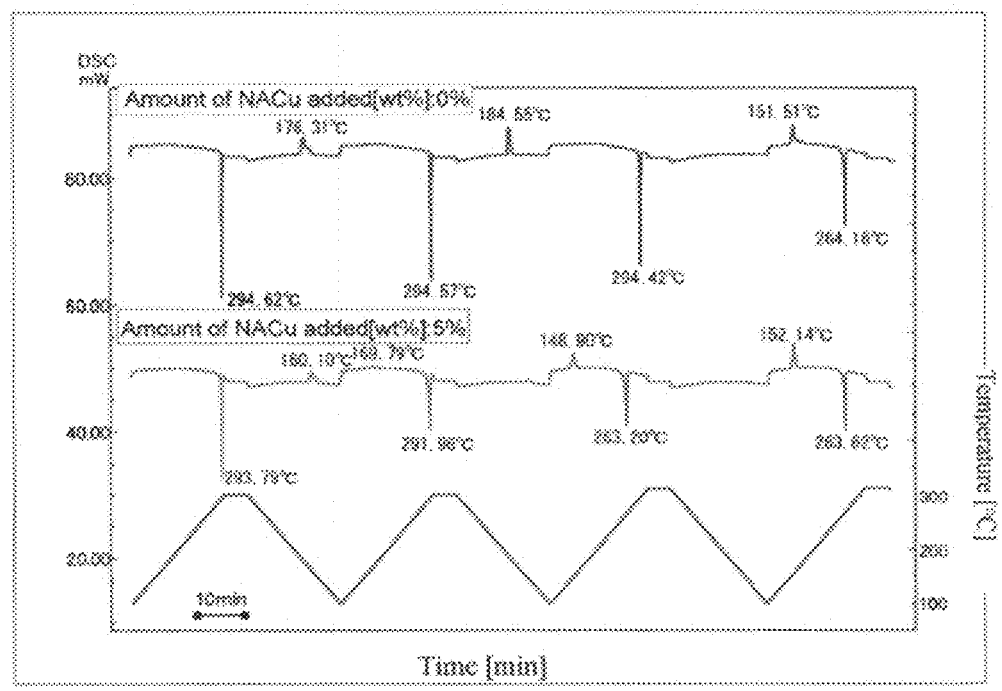
FIG. 19 shows in the upper part a DSC curve of a crude product of a complex compound NANi measured in a heating-cooling cycle indicated by a polygonal line in the lower part, and shows in the middle part a DSC curve of a mixture obtained by adding thereto 5% of a purified product of a complex compound NACu.

5% of a purified product of a complex compound NACu was added to a crude product of a complex compound NANi to result in a mixture, for which DSC measurement was carried out. The result thereof is shown in FIG. 19.

In this result, it was confirmed that, while the crude product of the complex compound NANi expressed a heat storage phenomenon from the third cycle, it was expressed from the second cycle with the addition of the purified product of the complex compound NACu.

[DSC Measurement Under Continuous Operation of Heating-Cooling Cycle]

Figure 20:
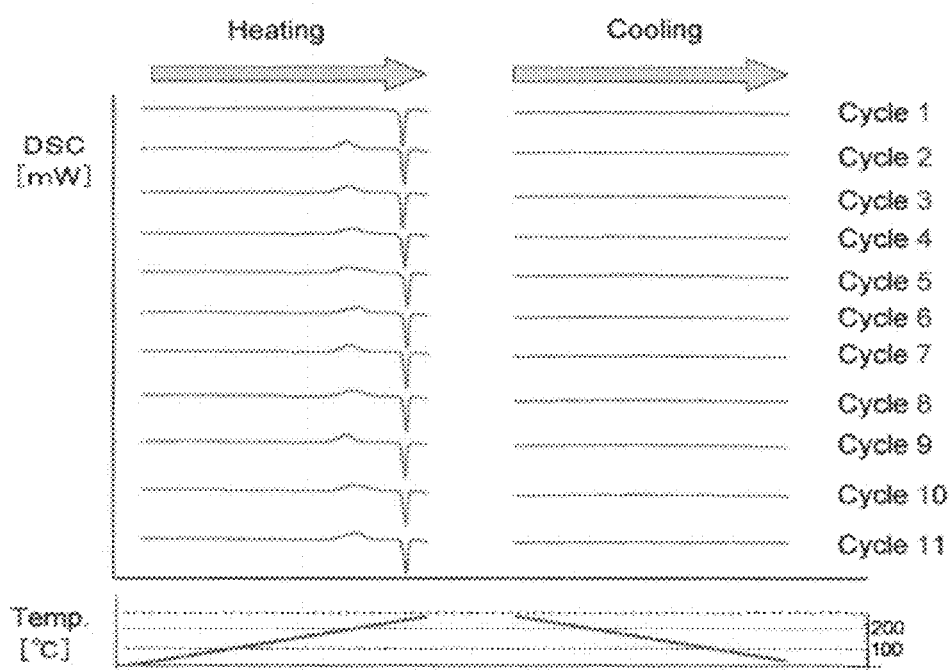
FIG. 20 shows in the upper part each DSC curve of a purified product of a complex compound NMTNi measured in each heating-cooling cycle indicated by a polygonal line in the bottom part.
Figure 21:
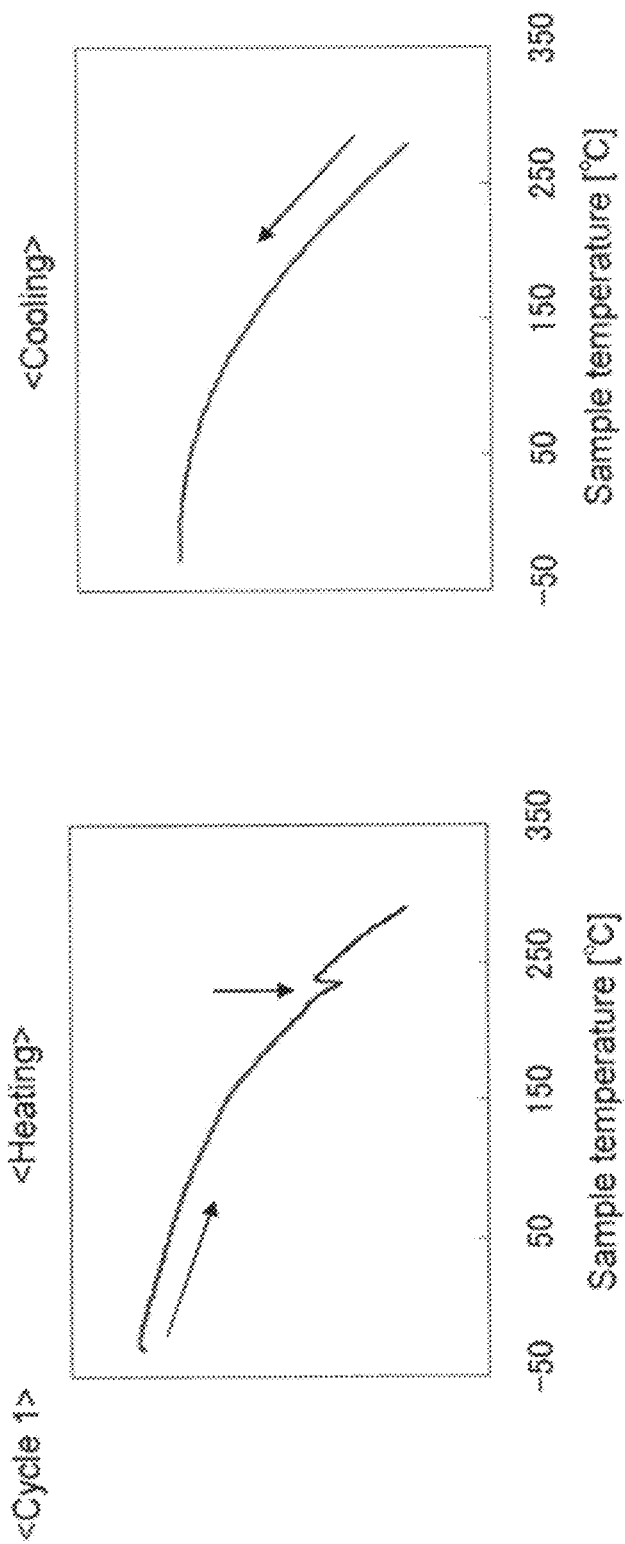
FIG. 21 shows DSC spectra of a crude product of a complex compound NACu during Cycle 1. In the diagrams, diagonal arrows indicate a direction of change in temperature, and a vertical arrow indicates a peak.
Figure 22:
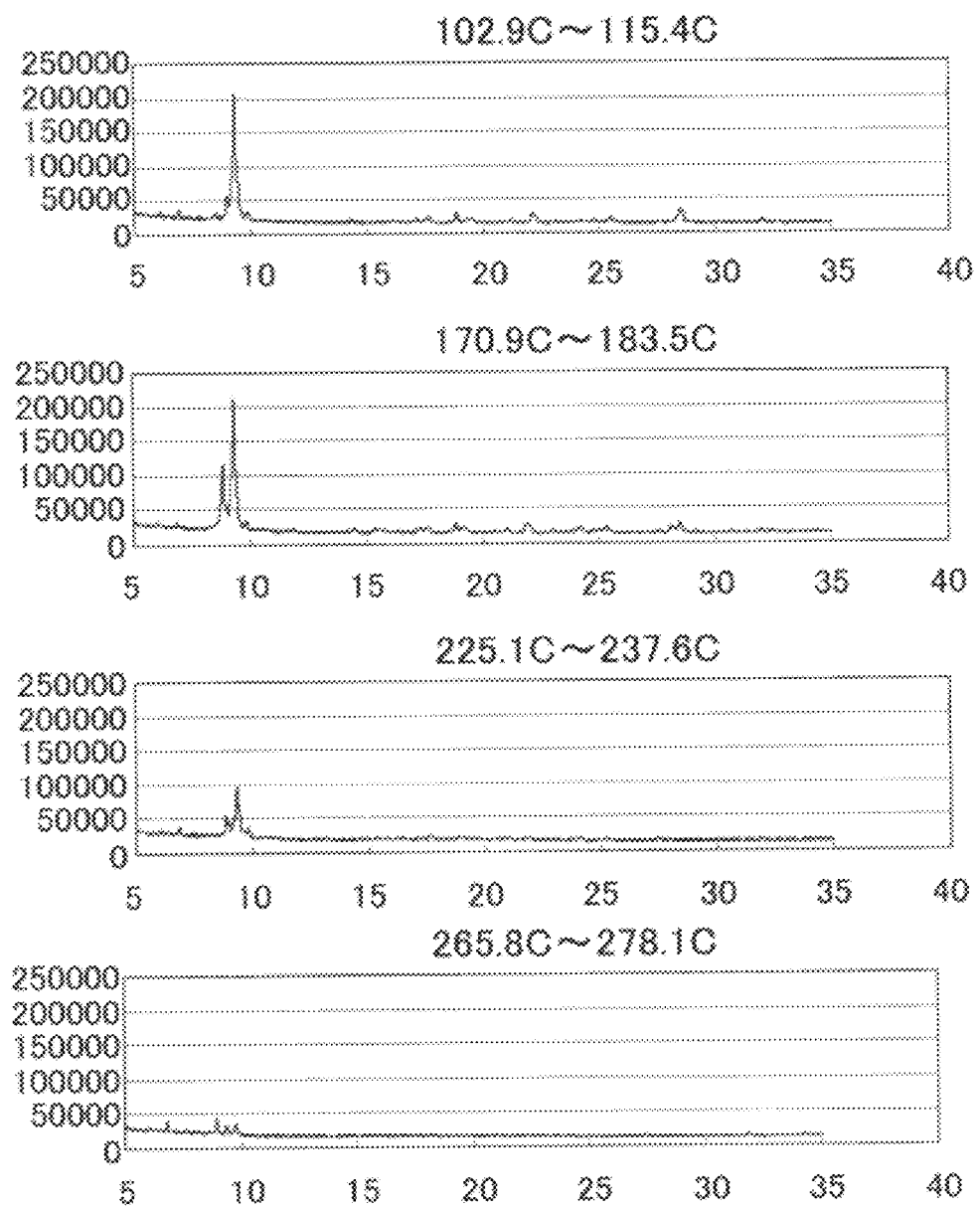
FIG. 22 shows powder X-ray diffraction spectra of a crude product of a complex compound NACu at each temperature during Cycle 1.
Figure 23:
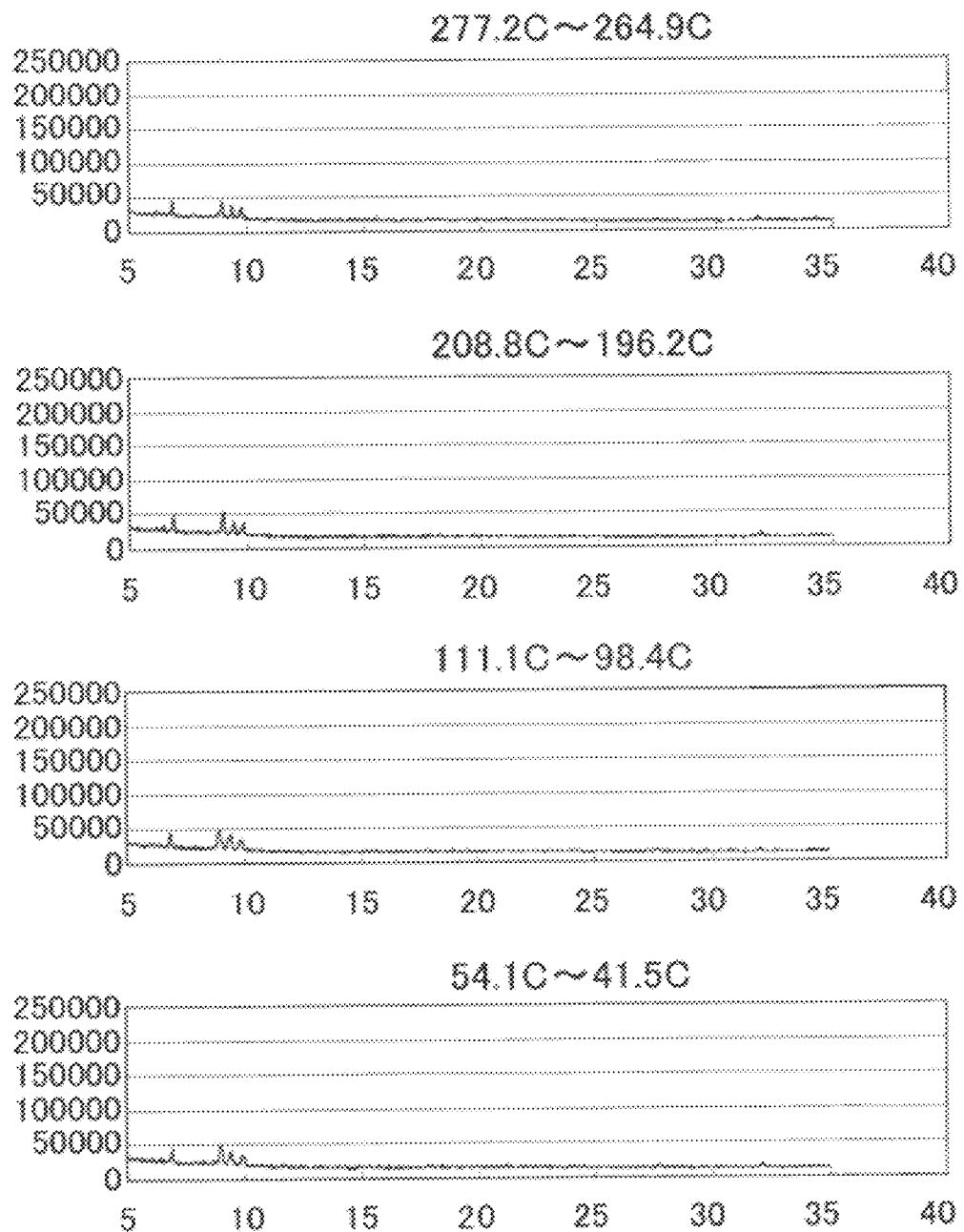
FIG. 23 shows powder X-ray diffraction spectra of a crude product of a complex compound NACu at each temperature during Cycle 1.
Figure 24:
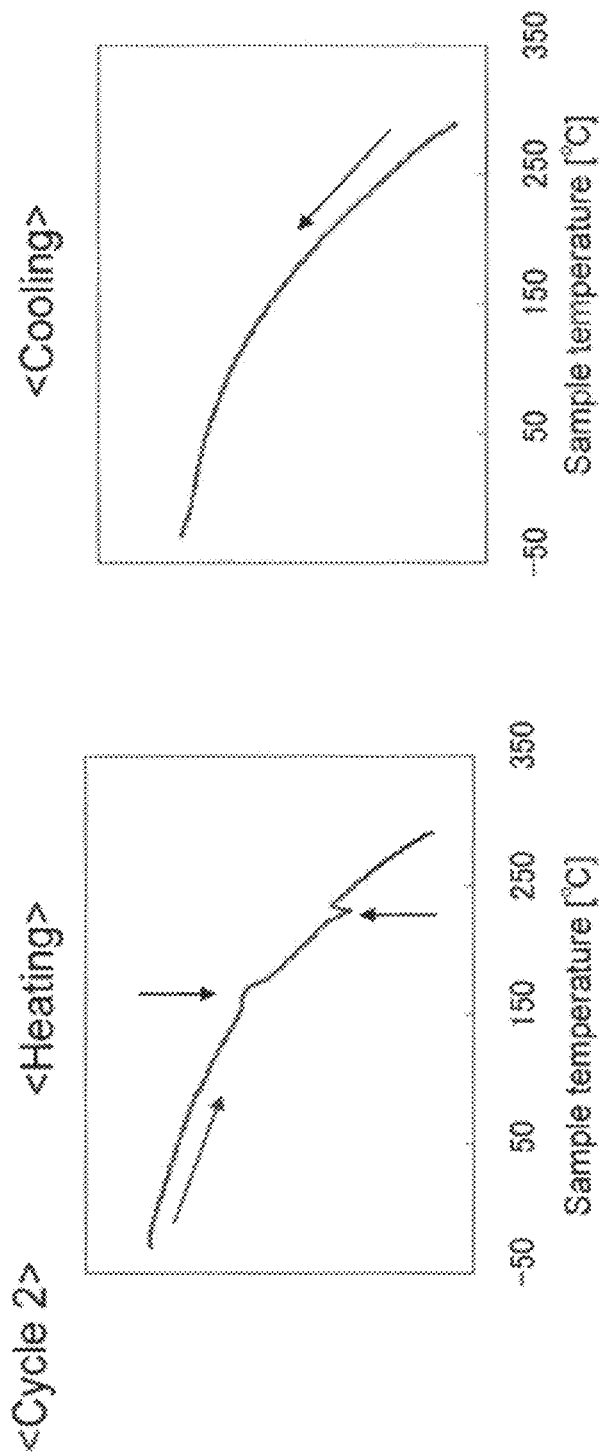
FIG. 24 shows DSC spectra of a crude product of a complex compound NACu during Cycle 2. In the diagrams, diagonal arrows indicate a direction of change in temperature, and vertical arrows indicate a peak.
Figure 25:
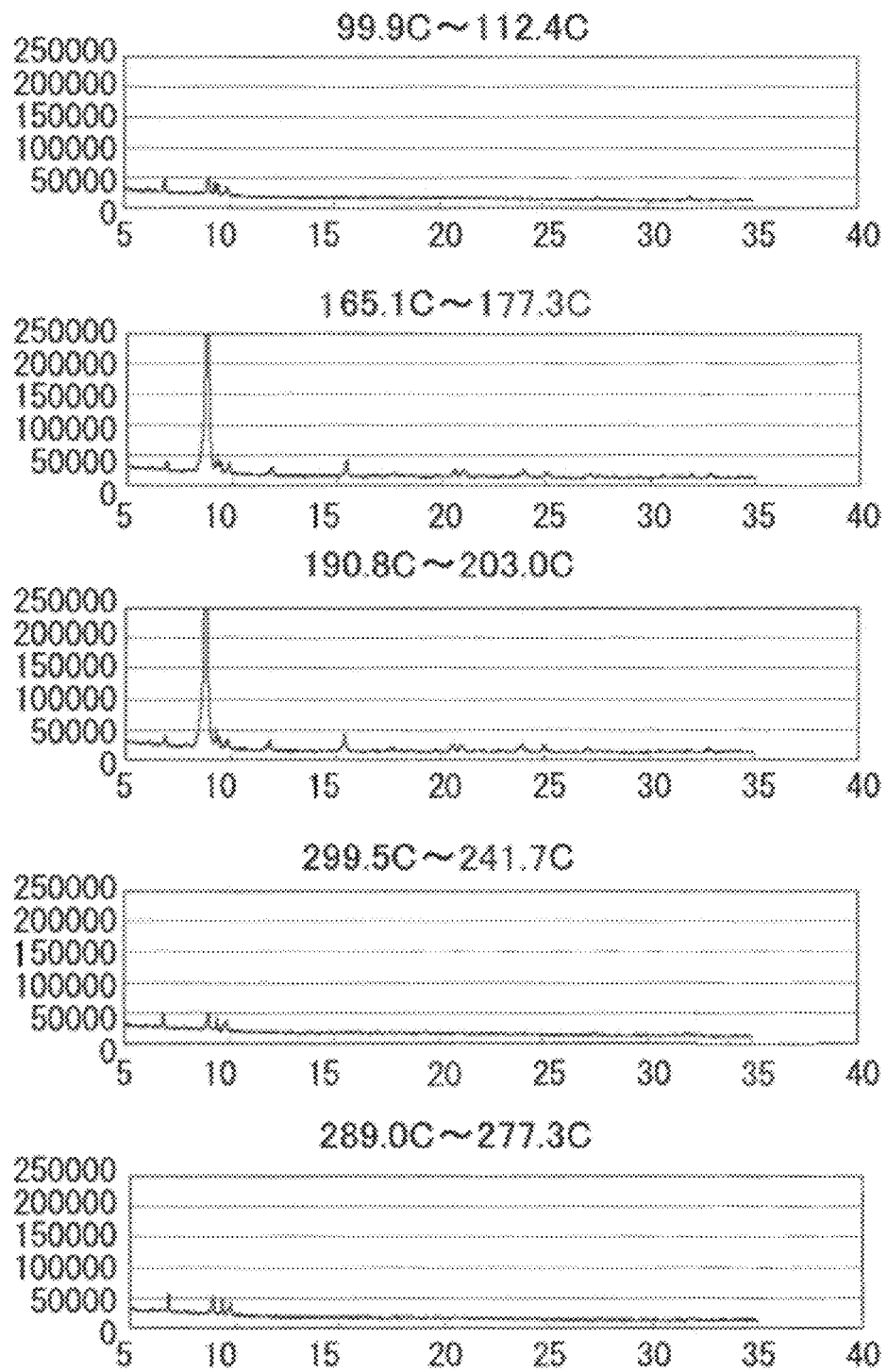
FIG. 25 shows powder X-ray diffraction spectra of a crude product of a complex compound NACu at each temperature during Cycle 2.
Figure 26:
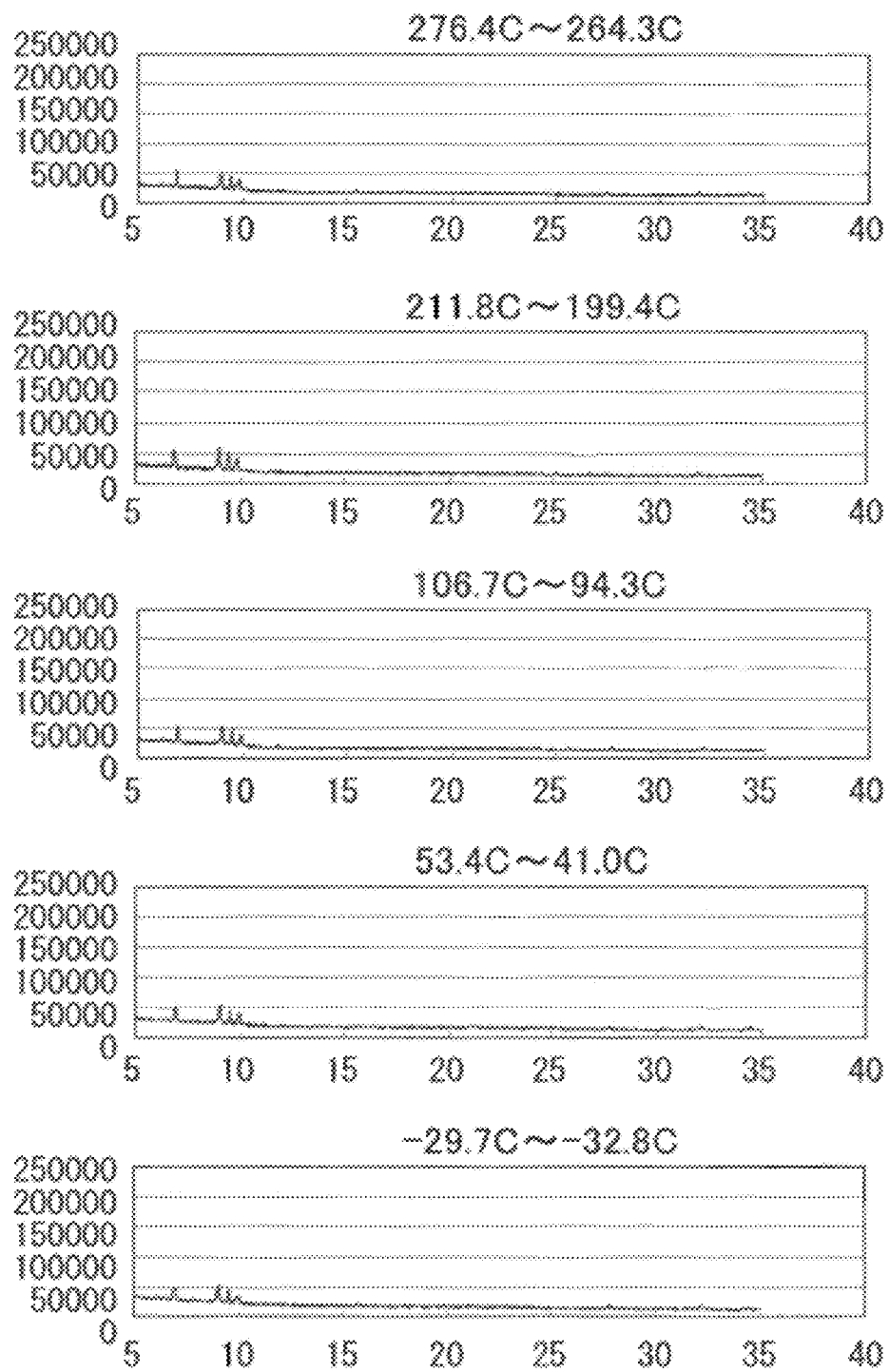
FIG. 26 shows powder X-ray diffraction spectra of a crude product of a complex compound NACu at each temperature during Cycle 2.
Figure 27:
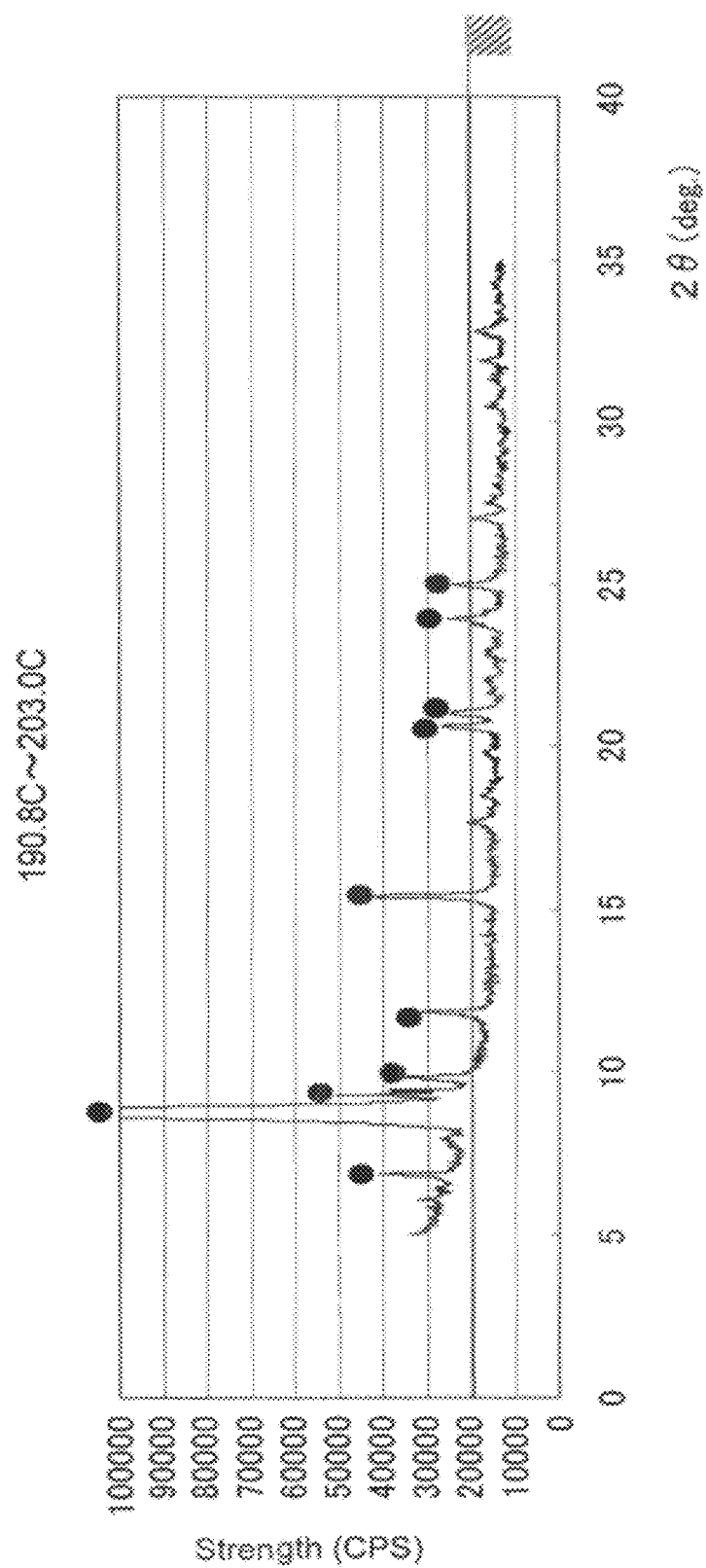
FIG. 27 shows a powder X-ray diffraction spectrum of a crude product of a complex compound NACu at 190.8° C. to 203.0° C. during Cycle 2. Circles in the diagram indicate a peak.
Figure 28:
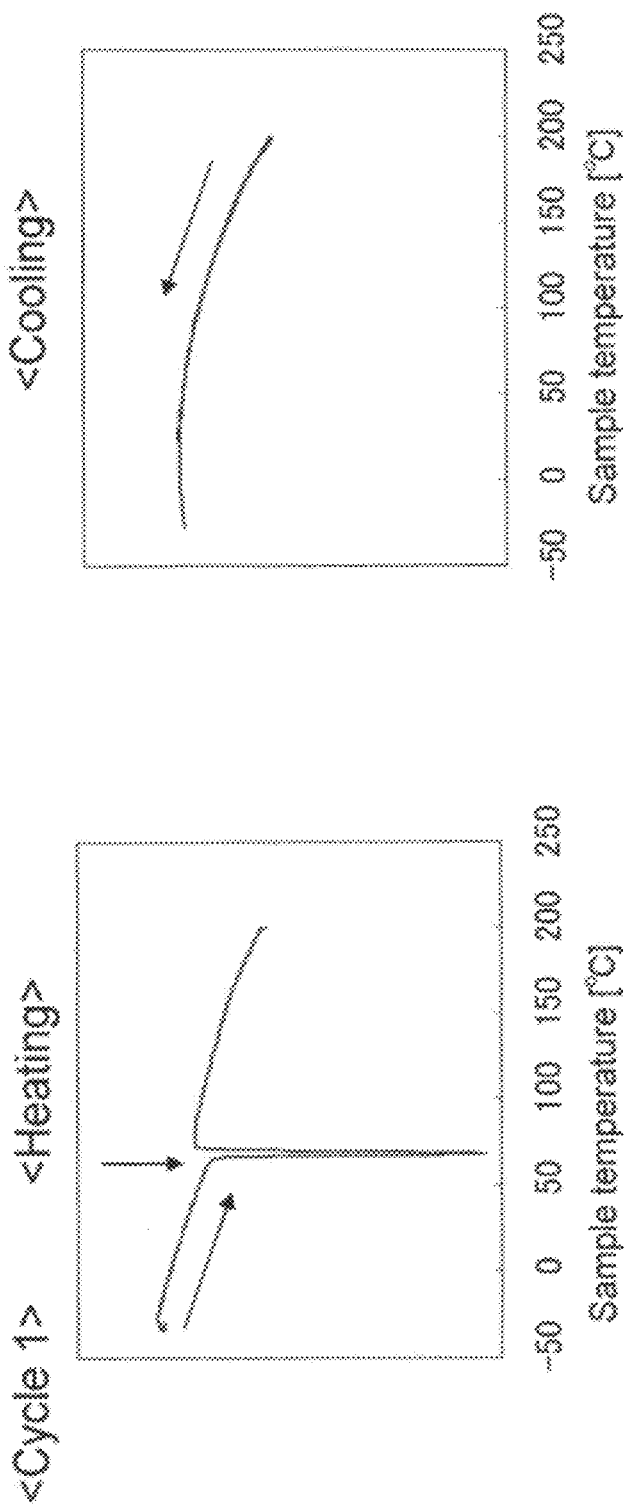
FIG. 28 shows DSC spectra of a complex compound S8Cu during Cycle 1. In the diagrams, diagonal arrows indicate a direction of change in temperature, and a vertical arrow indicates a peak.
Figure 29:
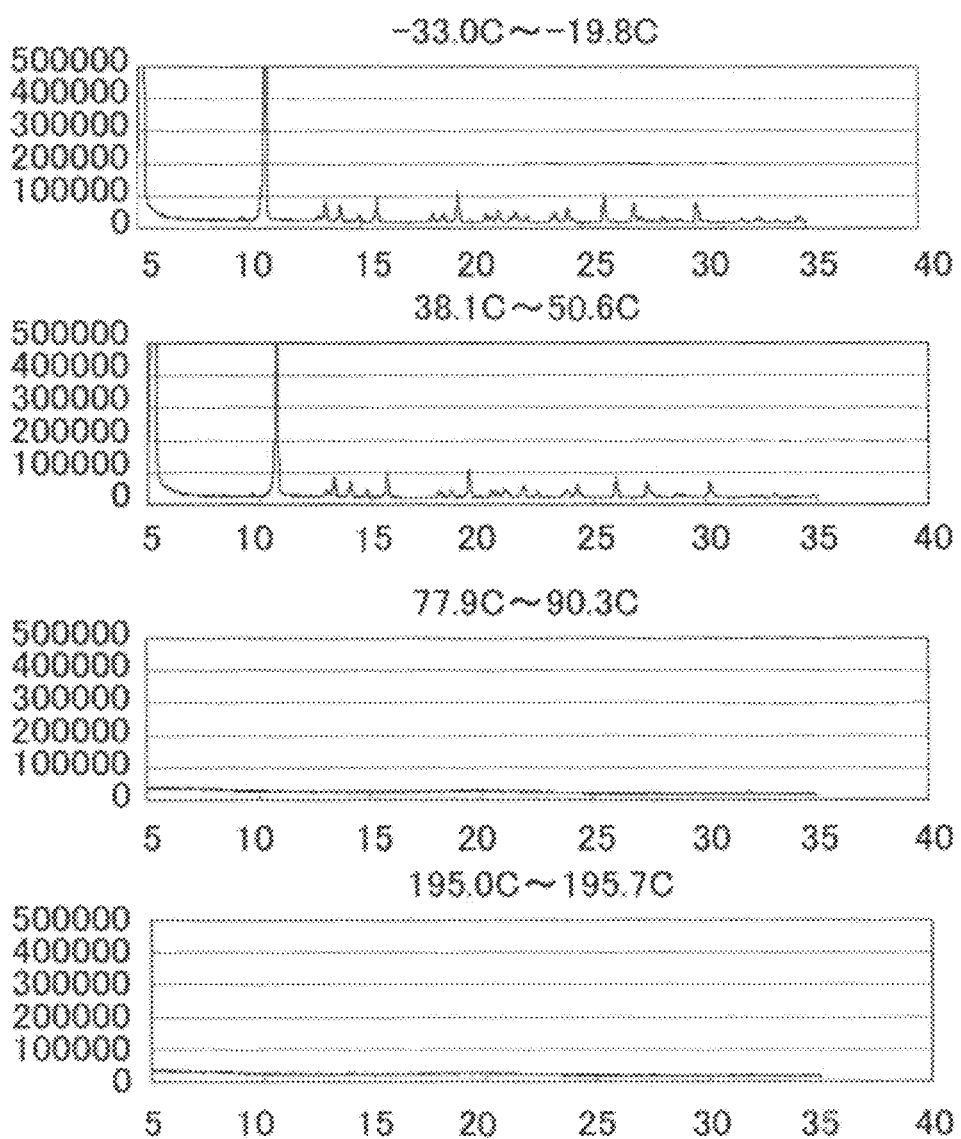
FIG. 29 shows powder X-ray diffraction spectra of a complex compound S8Cu at each temperature during Cycle 1.
Figure 30:
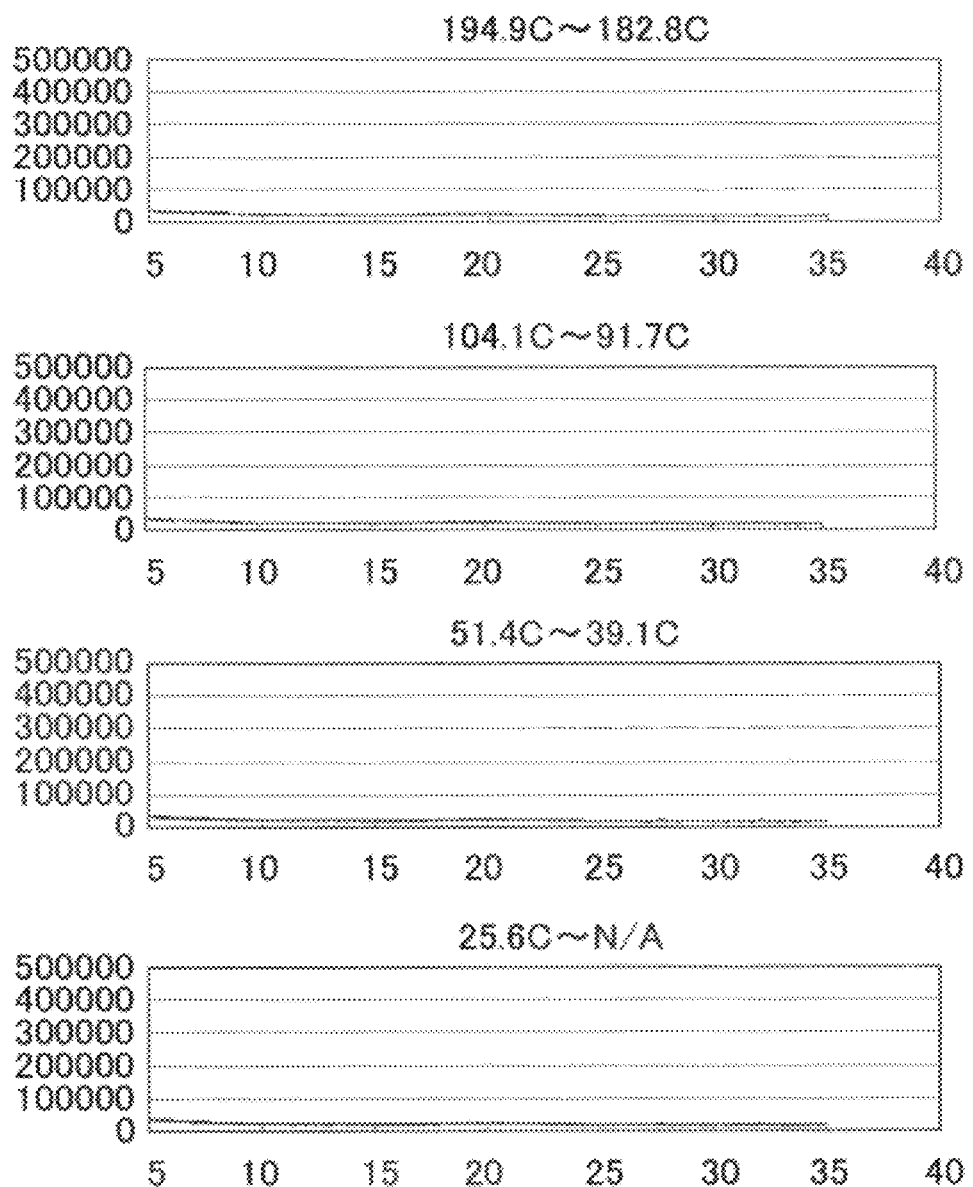
FIG. 30 shows powder X-ray diffraction spectra of a complex compound S8Cu at each temperature during Cycle 1.
Figure 31:
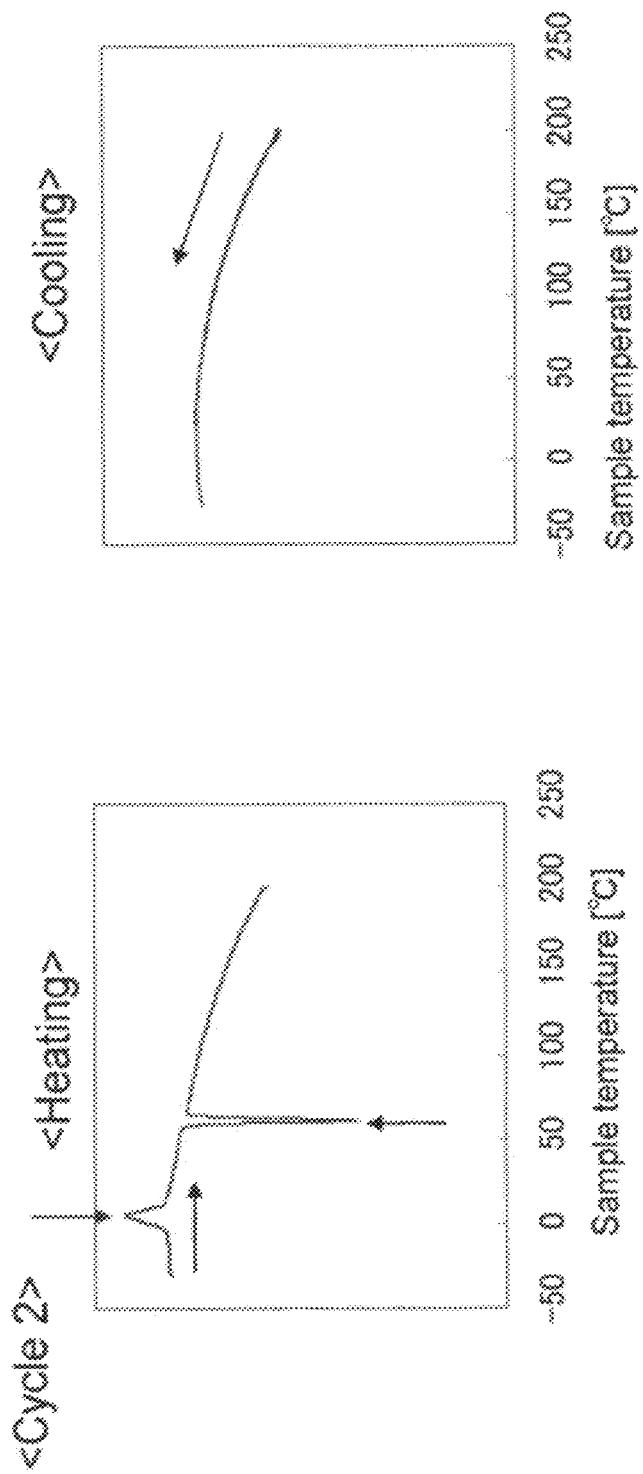
FIG. 31 shows DSC spectra of a complex compound S8Cu during Cycle 2. In the diagrams, horizontal and diagonal arrows indicate a direction of change in temperature, and vertical arrows indicate a peak.
Figure 32:
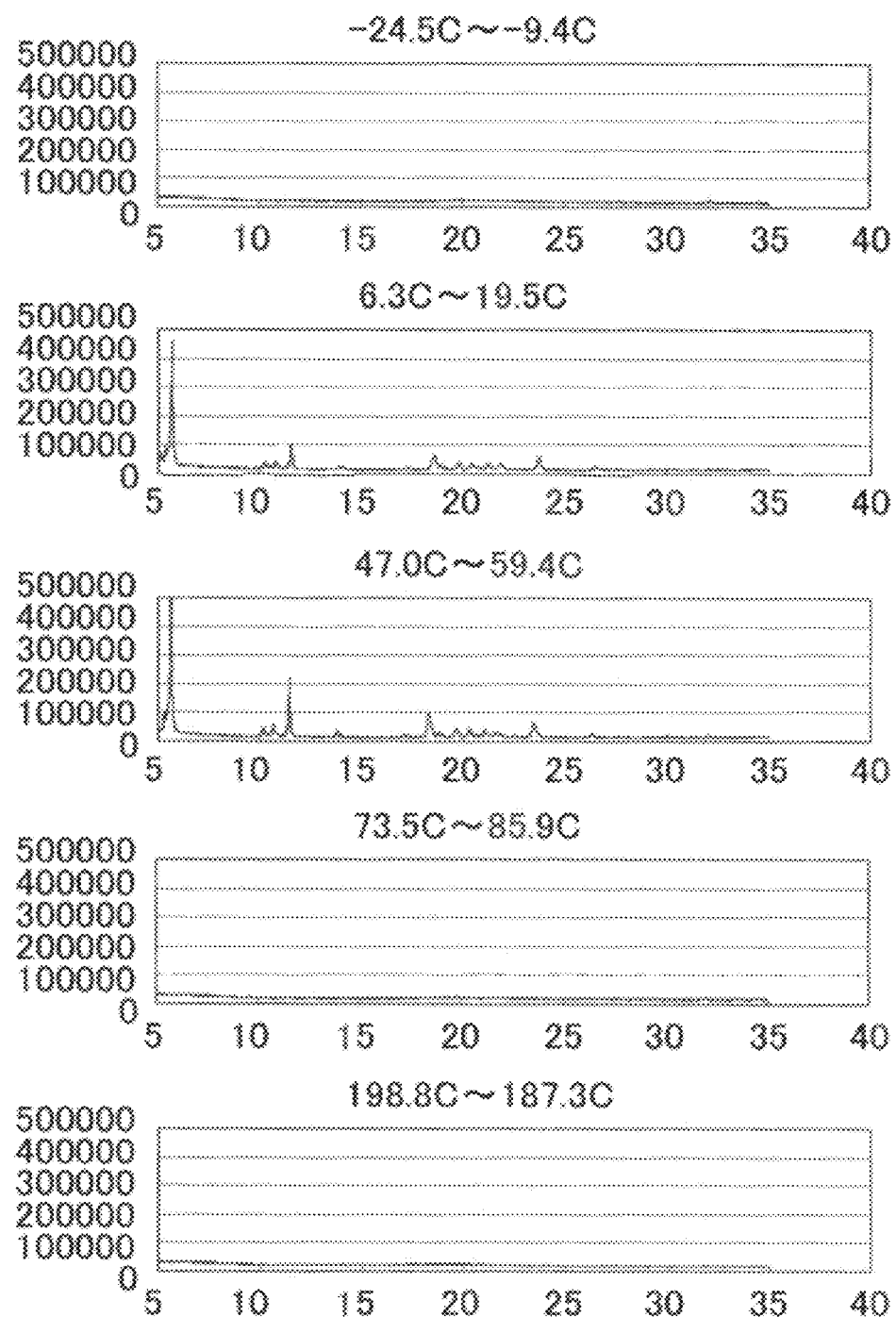
FIG. 32 shows powder X-ray diffraction spectra of a complex compound S8Cu at each temperature during Cycle 2.
Figure 33:
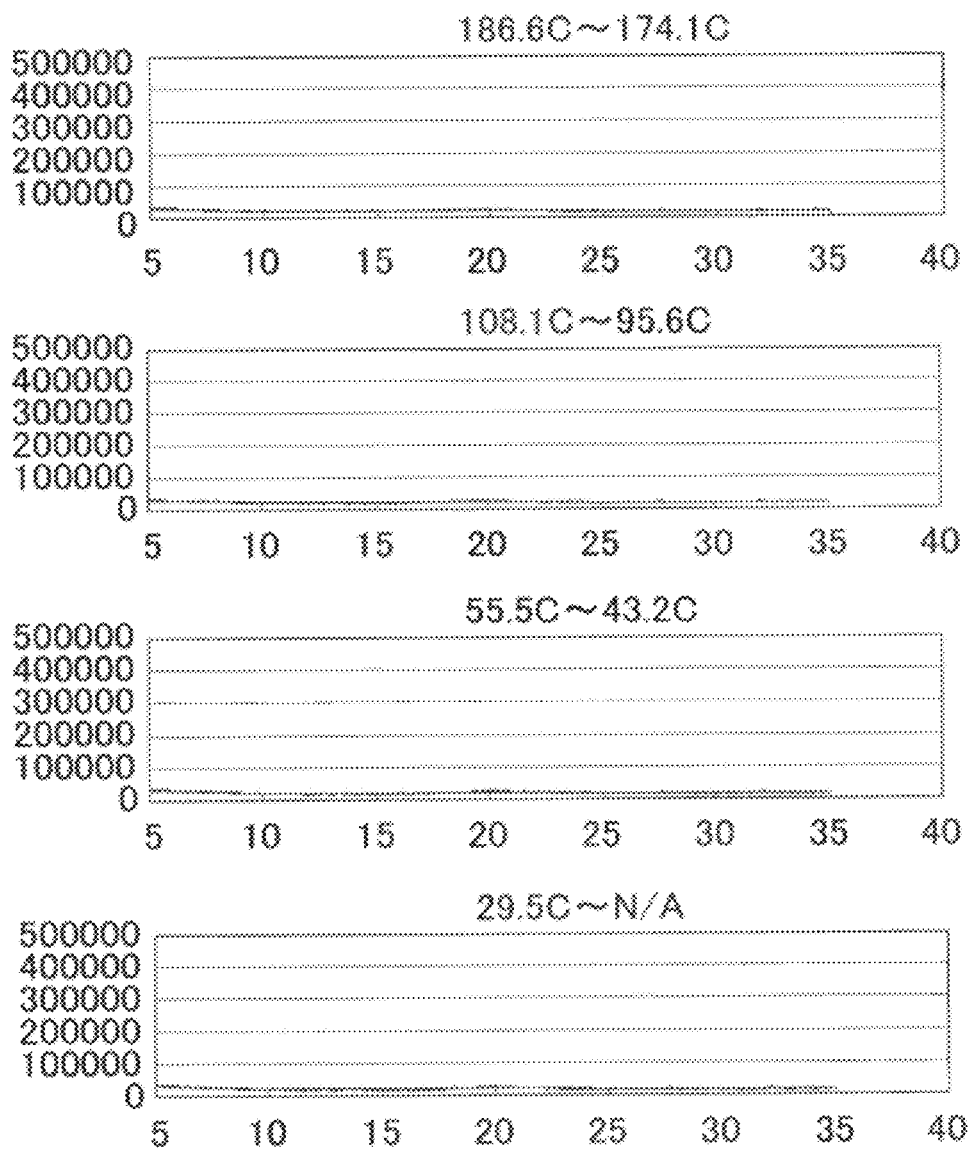
FIG. 33 shows powder X-ray diffraction spectra of a complex compound S8Cu at each temperature during Cycle 2.

A heating-cooling cycle was repeated in a plurality of times to carry out DSC measurement for a purified product of a complex compound NMTNi. The result thereof is shown in FIG. 20.

In this result, the expression of a heat storage phenomenon was confirmed up to Cycle 11.

[X-Ray Diffraction-Differential Scanning Calorimetry (X-Ray DSC) Simultaneous Measurement]

In the present invention, X-ray DSC simultaneous measurement was carried out using the following device and conditions.

Device: X-ray diffraction—differential scanning calorimetry simultaneous measurement device, Thermo plus EvoII (SmartLab (9 KW)), Rigaku Corporation <Device Configuration>

X-ray source: Cu—Kα

Light source system: focusing optical system (Reflection method)

Entrance side slit system:

Solar slit . . . 5 deg., Length limiting slit . . . 5 mm,

Entrance slit (IS) . . . ¼ deg.

Attachment: XRD-DSC attachment

Receiving side optical system:

Solar slit . . . 5 deg., Receiving slit 1 (RS1) . . . 8 mm,

Receiving slit 2 (RS2) . . . 13 mm

Detector: High-speed one-dimensional X-ray detector (D/teX Ultra)

<Scan Condition>

Tube voltage/tube current: 45 kV-200 mA

Scan axis: 2Θ-Θ

Operation method: continuous

Scan range: 5 to 35 deg.

Measurement time: 40 deg./min.

Sample interval: 0.02 deg.

<DSC Condition>

Speed of temperature rise: 10° C./min.

Atmospheric gas: $N_2$ (50 ml/min.)

Cooling: Circulation for low temperature

The complex compounds NACu (crude product) and S8Cu produced in the aforementioned Examples 1 and 2 were dried and about 5 to 10 mg thereof were weighed to carry out X-ray DSC simultaneous measurement. A step of once heating and then cooling back to the original temperature is defined as one cycle. The results of DSC spectra and powder X-ray diffraction spectra at each temperature in Cycle 1 and Cycle 2 are shown in FIGS. 21 to 34.

Figures 10A, 10B:
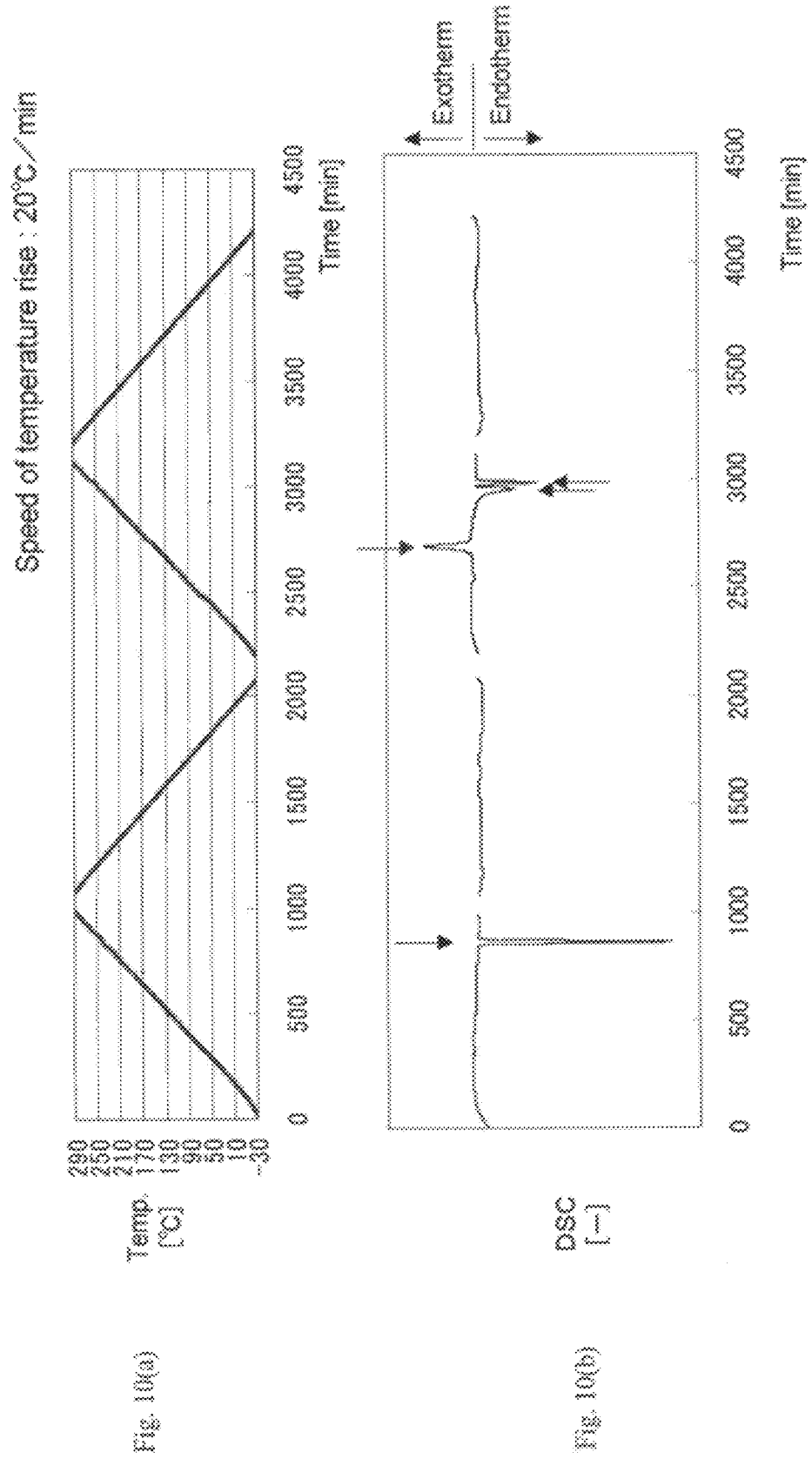
FIG. 10 ($a$) shows a heating-cooling cycle, and FIG. 10 ($b$) shows a DSC curve of a crude product of a complex compound NACu measured in this cycle.
Figure 11A:
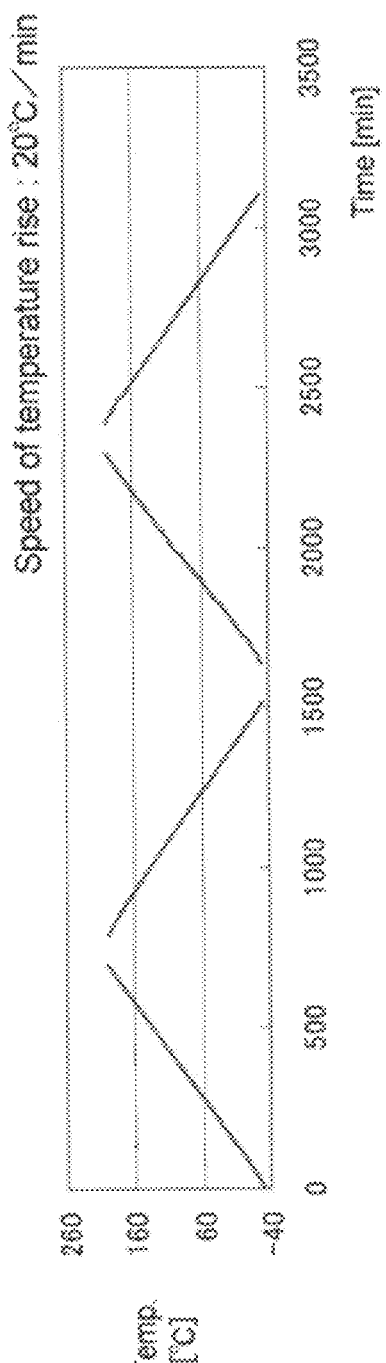
FIG. 11 ($a$) shows a heating-cooling cycle, and FIG. 11 ($b$) shows a DSC curve of a complex compound S8Cu measured in this cycle.
Figure 11B:
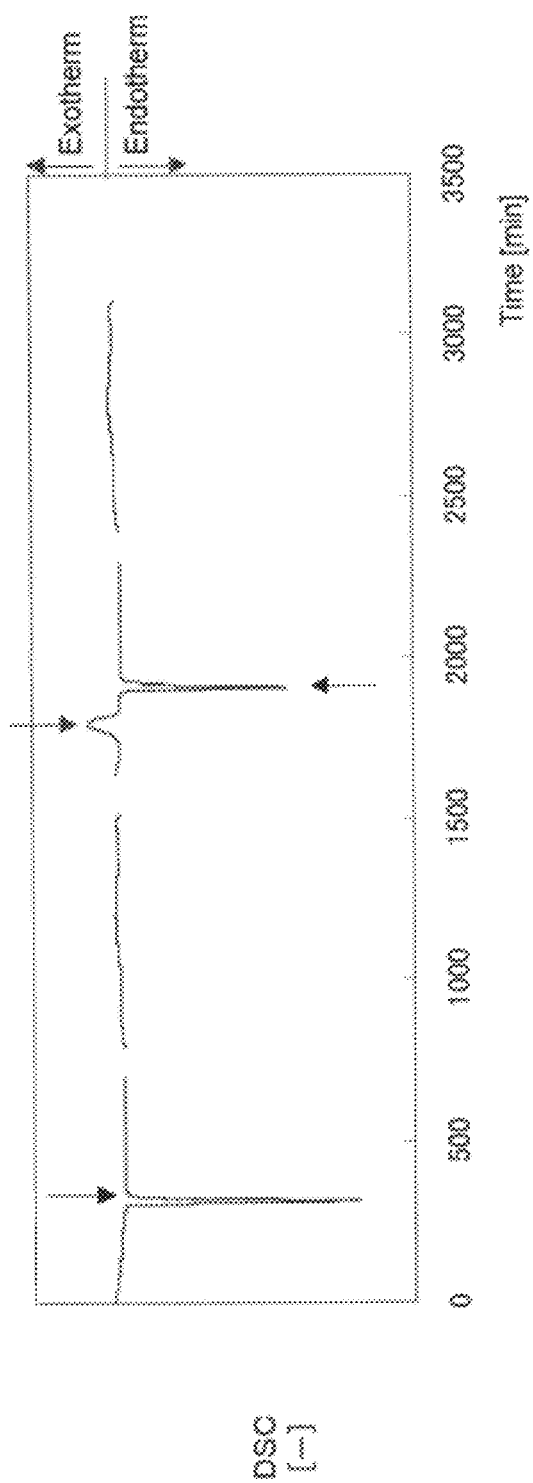
Figure 12:
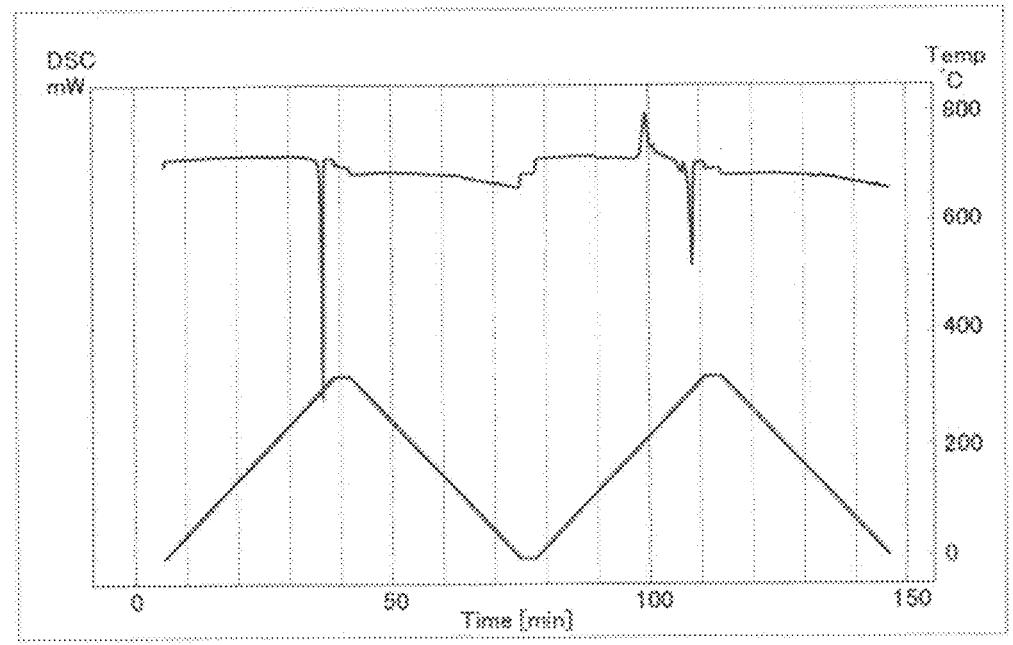
FIG. 12 shows in the upper part a DSC curve of a crude product of a complex compound NBPNi measured in a heating-cooling cycle indicated by a polygonal line in the lower part.
Figure 13:
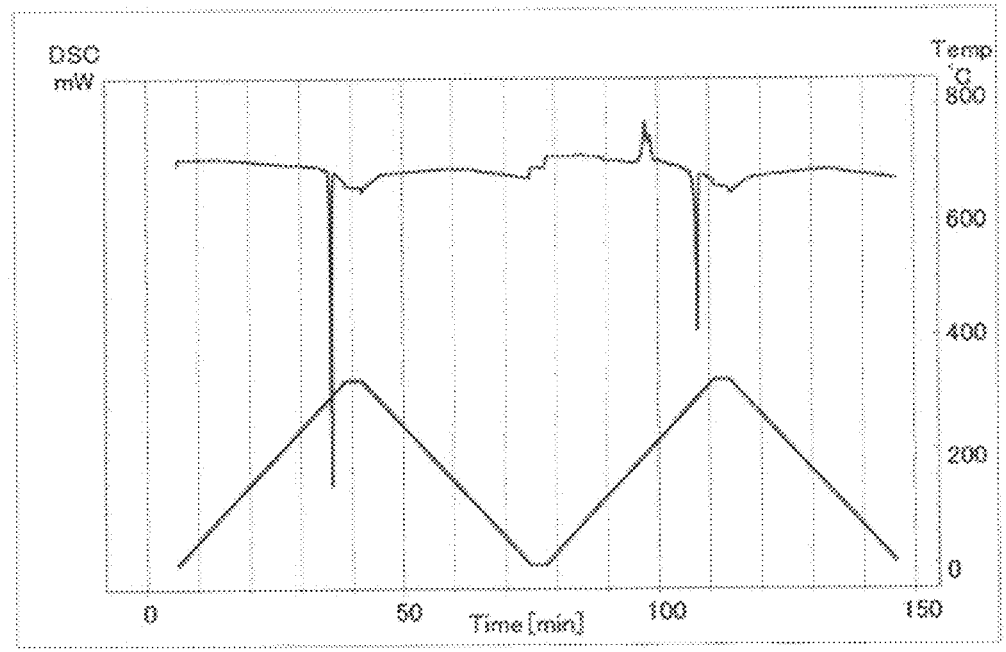
FIG. 13 shows in the upper part a DSC curve of a purified product of a complex compound NOTNi measured in a heating-cooling cycle indicated by a polygonal line in the lower part.
Figure 14:
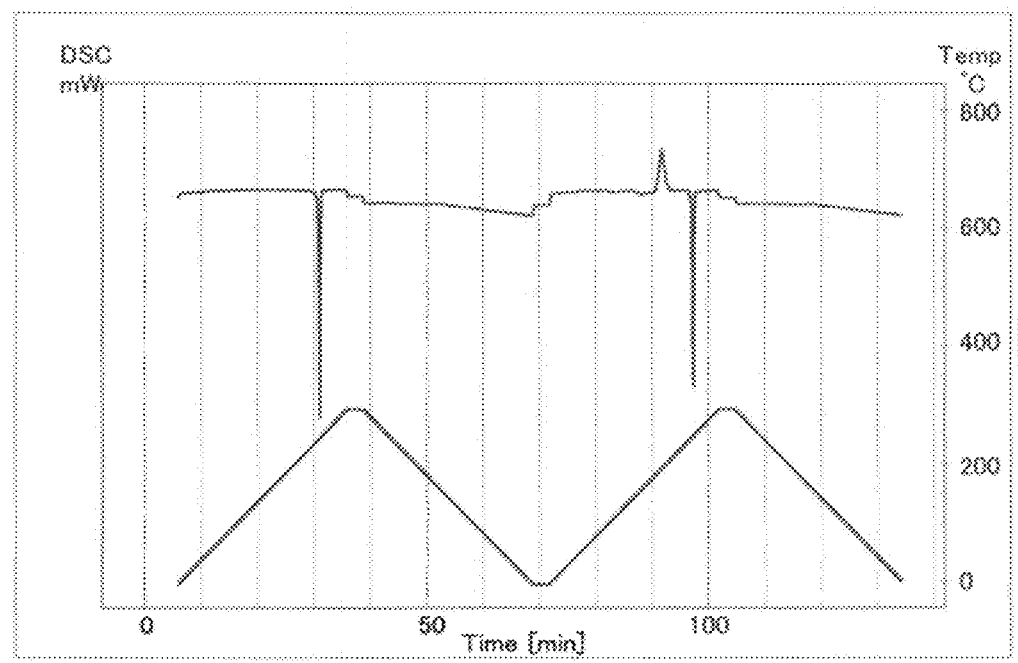
FIG. 14 shows in the upper part a DSC curve of a purified product of a complex compound NMTNi measured in a heating-cooling cycle indicated by a polygonal line in the lower part.

From DSC results, endothermic/exothermic behaviors of the complex compounds NACu and S8Cu were similar to those as in FIGS. 10 and 11. Further, from powder X-ray diffraction spectra measured simultaneously, non-crystallization (amorphous) has taken place after endothermic peak. On the other hand, from the fact that a multitude of sharp spectra are found after exothermic peak, it can be confirmed that crystallization has taken place.

Accordingly, it is suggested that the heat storage effect in the heat storage material of the present invention is to maintain the meta-stabilized (supercooled) state of an amorphous product after melting. Although the mechanism of the heat storage effect is not necessarily clear, it is considered that this is caused by the difference in molecular conformation and the like between crystallized state and melted (amorphous) state. It should be noted that a phenomenon similar to these was confirmed even when the aforementioned cycle was repeated 10 times (FIG. 20). From the above, it can be understood that the compound of the formula (I) changes its crystal structure to absorb/generate heat, i.e., store heat.

Bragg angle indicating a peak in a powder X-ray diffraction spectrum of the complex compound NACu at 190.8° C. to 203.0° C. demonstrating a heat storage effect in Cycle 2 is shown in the following table. After releasing energy stored, the complex compound NACu comes to have this diffraction pattern. That is, this diffraction pattern can be said to be a pattern specific to the complex compound NACu having a heat storage effect.

TABLE 1

| Bragg angle($2\theta \pm 0.1$) |
| --- |
| 6.9 |
| 8.9 |
| 9.3 |
| 9.8 |
| 11.8 |
| 15.4 |
| 20.6 |
| 22.0 |
| 24.0 |
| 25.0 |

Bragg angle having a peak in a powder X-ray diffraction spectrum of the complex compound S8Cu at 47.0° C. to 59.4° C. demonstrating a heat storage effect in Cycle 2 is shown in the following table. After releasing energy stored, the complex compound S8Cu comes to have this diffraction pattern. That is, this diffraction pattern can be said to be a pattern specific to the complex compound S8Cu having a heat storage effect.

TABLE 2

| Bragg angle($2\theta \pm 0.1$) |
| --- |
| 5.3 |
| 10.2 |
| 10.7 |
| 11.4 |
| 13.8 |
| 18.3 |
| 18.4 |
| 19.7 |
| 20.3 |
| 21.1 |
| 21.6 |
| 23.5 |

INDUSTRIAL APPLICABILITY

The heat storage material of the present invention can be utilized for an exhaust heat utilization system for vehicles, a heat utilization system for housing (e.g., air-conditioning system), or the like.

The invention claimed is:

1. A crystal of the formula:

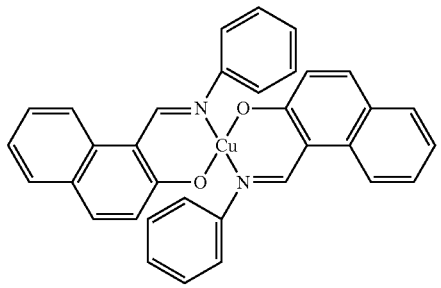

wherein the crystal has the following peaks at a Bragg angle:

| Bragg angle($2\theta \pm 0.1$) |
| --- |
| 6.9 |
| 8.9 |
| 9.3 |
| 9.8 |
| 11.8 |
| 15.4 |
| 20.6 |
| 22.0 |
| 24.0 |
| 25.0 | in a powder X-ray diffraction spectrum.

2. A method for storing thermal energy from a thermal energy source, comprising providing the thermal energy from the source to a complex compound such that the thermal energy is absorbed and stored in the complex compound, wherein the complex compound is a crystal of the formula:

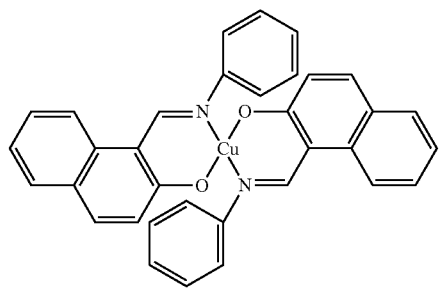
wherein the crystal has the following peaks at a Bragg angle:
| Bragg angle(2θ ± 0.1) |
| --- |
| 6.9 |
| 8.9 |
| 9.3 |
| 9.8 |
| 11.8 |
| 15.4 |
| 20.6 |
| 22.0 |
| 24.0 |
| 25.0 |
in a powder X-ray diffraction spectrum.
* * * * *